United States Patent
Nishiguchi et al.

(10) Patent No.: US 7,157,618 B2
(45) Date of Patent: Jan. 2, 2007

(54) IMPARTMENT OF VIRUS-RESISTANCE WITH THE USE OF PLANT PROTEIN BINDING TO PLANT VIRUS TRANSPORT PROTEIN

(75) Inventors: Masamichi Nishiguchi, Tsukuba (JP); Hiroshi Nyunoya, Fuchu (JP); Yasuhiko Matsushita, Fuchu (JP)

(73) Assignee: National Institute of Agrobiological Sciences, Tsukuba (JP)

( * ) Notice: Subject to any disclaimer, the term of this patent is extended or adjusted under 35 U.S.C. 154(b) by 71 days.

(21) Appl. No.: 10/489,229

(22) PCT Filed: Sep. 10, 2001

(86) PCT No.: PCT/JP01/07858

§ 371 (c)(1),
(2), (4) Date: Mar. 10, 2004

(87) PCT Pub. No.: WO03/022039

PCT Pub. Date: Mar. 20, 2003

(65) Prior Publication Data

US 2005/0177900 A1   Aug. 11, 2005

(51) Int. Cl.
*C12N 15/09* (2006.01)
*C12N 15/29* (2006.01)
*C12N 15/82* (2006.01)
*A01H 5/00* (2006.01)

(52) U.S. Cl. .......... 800/279; 800/278; 800/317; 800/320.1; 800/317.3; 435/468; 435/69.1

(58) Field of Classification Search ........ 800/278, 800/279, 298, 306, 317, 288; 435/69.1, 468
See application file for complete search history.

(56) References Cited

U.S. PATENT DOCUMENTS 5,571,706 A * 11/1996 Baker et al. ........... 800/279

OTHER PUBLICATIONS

Matsushita, Y. et al., "The tomato mosaic tobamovirus movement protein interacts with a putative transcriptional coactivator KELP," *Molecules and Cells*, vol. 12, No. 1, pp. 57-66, (2001).
Kawakami, S. et al., "Shokubutsu Virus 2. Shokubutsu Virus no movement protein (MP) no meguru Wadai," *Virus*, vol. 49, No. 2, pp. 107-118, (1999).
Soellick, T. et al., "The movement protein NSm of tomato spotted wilt tospovirus (TSWV): RNA binding, interaction with the TSWV N protein, and identification of interacting plant proteins," *Proc. Natl. Acad. Sci. USA*, vol. 97, No. 5 pp. 2373-2378, (2000).
Weber, H. et al., "Tm-$2^2$ resistance in tomato requires recognition of the carboxy terminus of the movement protein of tomato mosaic virus," *Mol. Plant Microbe Interact.*, vol. 11, No. 6, pp. 498-503, (1998).
Hall, T.J., "Resistance at the TM-2 Locus in the Tomato to Tomato Mosaic Virus," *Euphytica*, vol. 29, pp. 189-197, (1980).
Fraser, R.S.S., "The Genetics of Resistance to Plant Viruses," *Annu. Rev. Phytopathol.*, vol. 28, pp. 179-200, (1990).
Meshi, T. et al., "Mutations in the Tobacco Mosaic Virus 30-κd Protein Gene Oversome Tm-2 Resistance in Tomato," *The Plant Cell*, vol. 1, pp. 515-522, (1989).
Weber, H. et al., Two Amino Acid Substitutions in the Tomato Mosaic Virus 30-Kilodalton Movement Protein Confer the Ability to Overcome the Tm-$2^2$ Resistance Gene in the Tomato, *Journal of Virology*, vol. 67, No. 11, pp. 6432-6438, (1993).

* cited by examiner

*Primary Examiner*—Medina A. Ibrahim
(74) *Attorney, Agent, or Firm*—Jacqueline F. Mahoney; Perkins Coie LLP

(57) ABSTRACT

A method for conferring resistance to a plant virus to plants by introducing into the plant a polynucleotide encoding a protein capable of binding to a movement protein of the plant virus is provided. Also provided are transgenic plants having resistance to a plant virus.

7 Claims, 13 Drawing Sheets

FIG. 2

Figure 1:
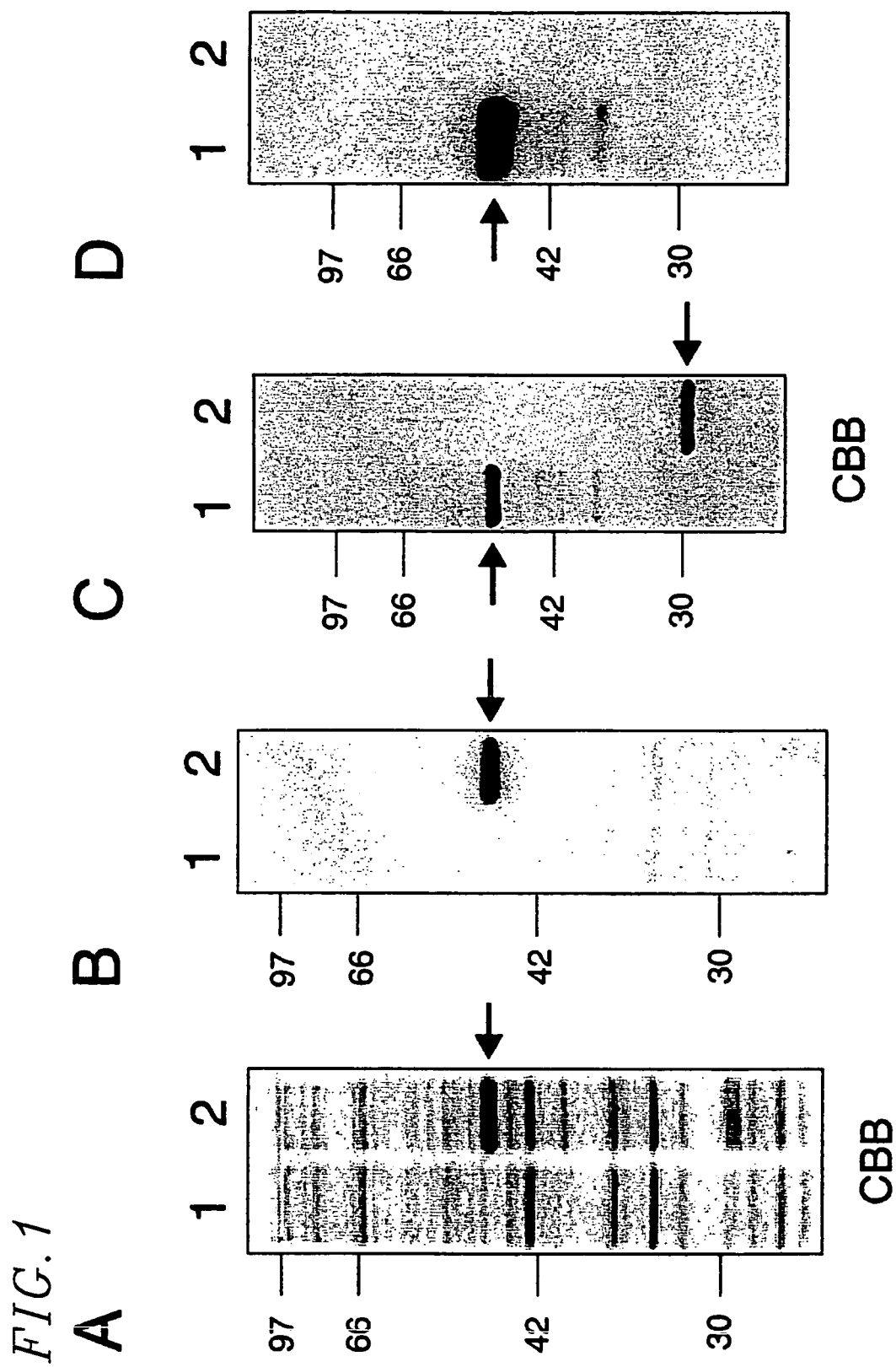

```
GAAAACCCTAAAGATGGAGGAAGAAAGCAAGGCGAAGATCGAGGAAACGGTGCGAGAGAT  60
              M  E  E  E  S  K  A  K  I  E  E  T  V  R  E  I

TCTGAAGGAATCGGACATGACGGAGATGACAGAGTTCAAGGTCCGTAACCTCGCTTCGGA  120
 L  K  E  S  D  M  T  E  M  T  E  F  K  V  R  N  L  A  S  E

GAGACTCGGCATCGATCTCTCAGACAAATCTCACAAGGCGTTCGTACGCGGCATCGTCAA  180
 R  L  G  I  D  L  S  D  K  S  H  K  A  F  V  R  G  I  V  K

GTCGTTCCTCGAAGAAGTGGAGTCGAAACAACAACAACAACAGGACAAGGAAGAGGAAGA  240
  S  F  L  E  E  V  E  S  K  Q  Q  Q  Q  Q  D  K  E  E  E

GGAAGAAGAAGAAGAAAGAGCTAAGGAGGGAAACAAAGAGTTTGACGATGACGGCGATCT  300
 E  E  E  E  R  A  K  E  G  N  K  E  F  D  D  D  G  D  L
                               1
                               ▼
CATCATTTGCAGGCTGTCGGATAAGAGGAGAGTGACGATTCAGGAGTTTAGAGGAAAGAG  360
 I  I  C  R  L  S  D  K  R  R  V  T  I  Q  E  F  R  G  K  S
                                                          2
                                                          ▼
TTTGGTTTCCATCAGAGAGTATTACAAGAAAGACGGCAAAGAGCTTCCTTCTTCTAAAGG  420
 L  V  S  I  R  E  Y  Y  K  K  D  G  K  E  L  P  S  S  K  G

HindIII
AATAAGCTTAACAGACGAACAATGGTCAACGTTCAAGAAAAATATTCCAGCTATCGAAGC  480
    I  S  L  T  D  E  Q  W  S  F  K  K  N  I  P  A  I  E  A TGCTGTCAAGAAAATGGAATCGCGTGTCTGACGAACTTGTGGTTGATTCTGCTTTCAGAA  540
 A  V  K  K  M  E  S  R  V  *

ACATATGCAAGTGTCTTGTTGAATCAGTGGTGCAAAATGTTATTGTGTTTATGTAACTTA  600

TTTTCTTTCTTCGGTTGGTCGTAATGTGTTTCTAAGAGGACCTGGCGAACGAGCCACTAT  660

CATCAGAGTATTCAGTAGTACTTGGCCCTGTTCGTTTGCTCACCCAGGTGATCCATCTGG  720

GTGAAGATGCAAATTGATGTTCGTTTAGTGTATTATAATGCTACATCCAGATGAATCACC  780

EcoRI
CAGCTGAATTCATCTCAAATTCTCACCCAAATGAAGGTGAGTCTTGATGGTGCATCTGGA  840

TACAGATGCATCTAGTTCAGTCCAAAATAATAAATGACAAAAATGATCTTTTAAAATCAA  900

AAAAAAAAAAAAA                                                913
```

FIG. 3

```
MIP102         1:MEEESKAKIEETVREILKESDMTEMTEFKVRNLASERLGIDLSDKSHKAFVRGIV 55
                 ** * *   *** *  **** *****    * ****
A.thaliana KELP 1:MEKETKEKIEKTVIEILSESDMKEITEFKVRKLASEKLAIDLSEKSHKAFVRSVV 55

MIP102        56:KSFLEEVESKQQQQDKEEEEEERAKEGNKEFDDDGDLIICRLSDKRRVTIQ 110
                 ** *                    ******* ****************
A.thaliana KELP 56:EKFLDEERAREYENSQVNKEEEDGDKDCGKGNKEFDDDGDLIICRLSDKRRVTIQ 110

MIP102       111:EFRGKSLVSIREYYKKDGKELPSSKGISLTDEQWSTFKKNIPAIEAAVKKMESRV 165
                 ** ******************************* *** ***********
A.thaliana KELP 111:EFKGKSLVSIREYYKKDGKELPTSKGISLTDEQWSTFKKNMPAIENAVKKMESRV 165
```

```
MIP102                          117:LVSIREYYKK DG KELPSSKGISL 139
A.thaliana KELP                 117:LVSIREYYKK DG KELPTSKGISL 139
A.thaliana KIWI                  62:WIDIREFYVK DG KTLPGKKGISL  84
S.pombe (unknown ORF)            78:YVHIREYYEK DG DMLPGKKGIAL  72
C.elegans (unknown ORF)          81:YVNIREYYIDRDSQKMMPSRKGISL 105
Human (PC4/p15)                  82:LIDIREYWMDPEG EMKPGRKGISL 105
```

FIG.5
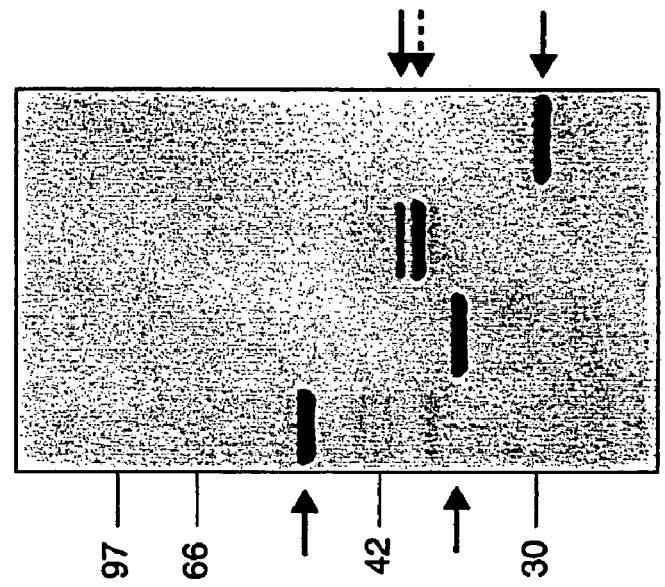
A
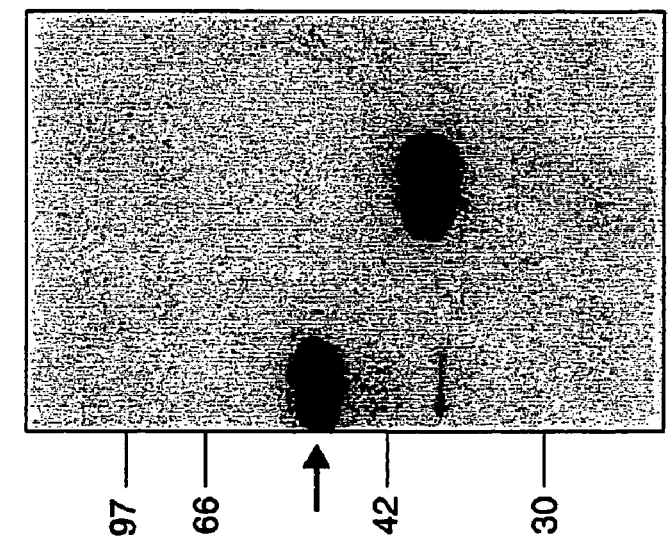
B CBB

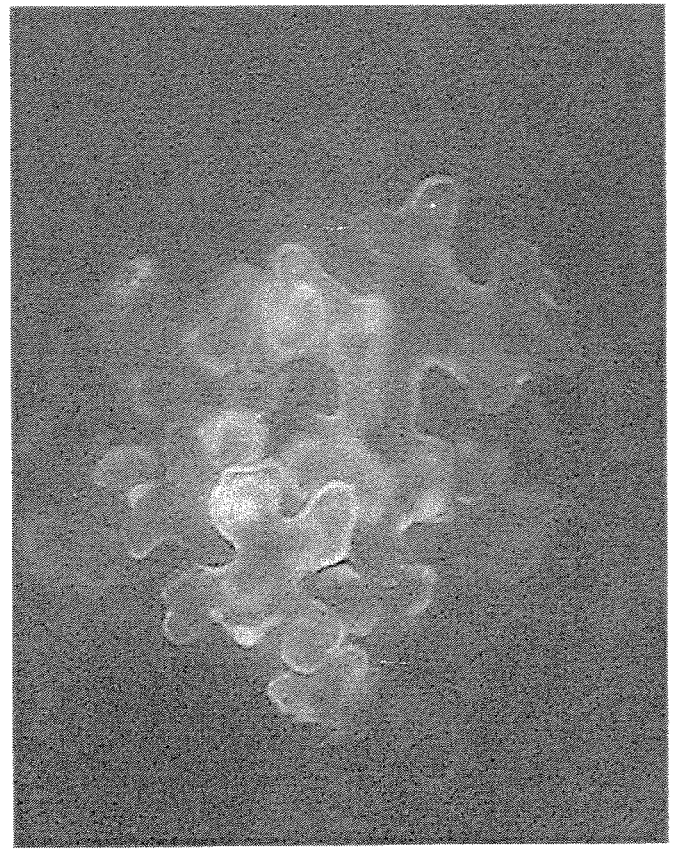
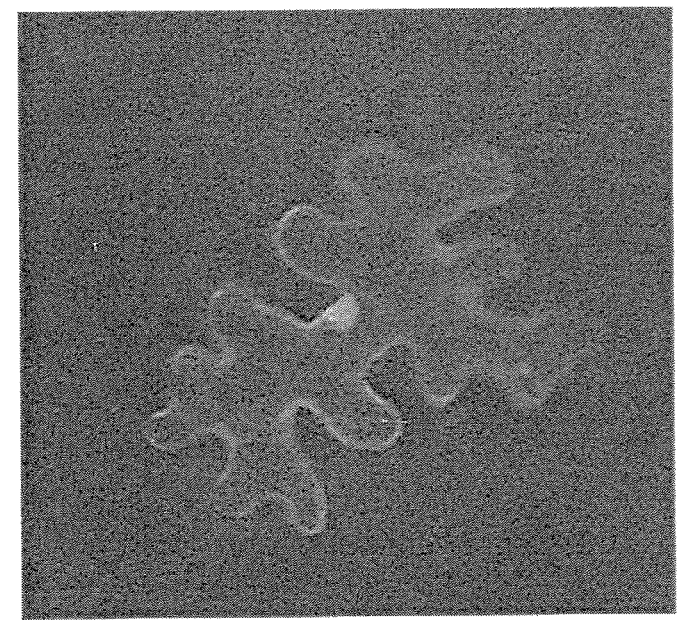
FIG. 6
One Cell
Multiple Cells pART27-Bc2dC-HA.a

FIG. 13

ToMV

CTMV-W

CMV

GST

BSA

IMPARTMENT OF VIRUS-RESISTANCE WITH THE USE OF PLANT PROTEIN BINDING TO PLANT VIRUS TRANSPORT PROTEIN

TECHNICAL FIELD

The present invention relates to a method for conferring plant virus resistance to plants. More preferably, the present invention relates to a method for conferring virus resistance to plants by expressing a protein capable of binding to a plant viral movement protein in plants.

BACKGROUND ART

Some molds and bacteria invade plants by secreting a cell wall-degrading enzyme or the like. In contrast, plant viruses, such as tobacco mosaic virus (TMV) and tomato mosaic virus (ToMV) belonging to plant RNA viruses, do not encode the gene of a cell wall-degrading enzyme or the like, and can go through cell walls only after entering through a physical scar or being transmitted by insects or fungi.

A highly infective virus, for example, tobacco mosaic virus, exhibits massive multiplication activity, such as production of $10^6$ progeny per day. Such a level of multiplication does not always lead to disease. Initially infected cells are only a part of a whole plant, and most cells are not invaded. In many cases, a cell on the surface of a leaf is first infected with a virus and the virus transfers into a mesophyll cell in which the virus is in turn multiplied. The multiplied viruses spread into the surrounding mesophyll cells. In this manner, viruses spread throughout plant tissue. Such a process of a plant virus spreading to neighboring cells is called cell-to-cell movement. Viruses move to vascular bundle sheath cells, sieve parenchyma, and then companion cells, and subsequently start to move from tissue to tissue through sieve elements. This movement is called long-distance movement (Saibo-Kogaku [Cellular Engineering], Special Issue, Syokubutu-Saibo-Kogaku [Plant Cellular Engineering] series, Vol. 8, Shujyunsha, pp. 146–155, Chapter 3 "Uirusu-Teikosei-no-tame-no-Senryaku [Strategy for Virus Resistance]", p. 2, Yuichiro Watanabe, "Syokubutsu-Uirusu-no-Saibokan-Iko [Cell-to-Cell Movement of Plant Virus]").

Examples of resistance reactions of host plants against viral infection are: (1) suppression of the amount of multiplication of a virus, or substantially no disease symptoms despite multiplication of a virus (tolerance); (2) multiplication of a virus only in a cell which the virus has first entered, and prevention of movement of the virus to surrounding cells so that the virus cannot spread throughout a plant (subliminal infection); (3) multiplication of a virus in an infected leaf, and suppression of long-distance movement from the infected leaf to upper leaves, resulting in no systemic infection; and (4) rapid necrosis of tissue at infection sites in an early stage of viral infection, resulting in local necrotic lesion. Viruses are localized within necrotic tissue or a surrounding portion thereof, thereby avoiding systemic infection (hypersensitive reaction). Based on these findings, efforts have been made to further elucidate resistance mechanisms. In the efforts, molecular research on virus resistance has been conducted by physiological and biochemical analysis and genetic analysis from view points of infecting viruses and host plants (Saibo-Kogaku [Cellular Engineering], Special Issue, Syokubutu-Saibo-Kogaku [Plant Cellular Engineering] series, Vol. 8, Shujyunsha, pp. 166–176, Chapter 3 "Uirusu-Teikosei-no-tame-no-Senryaku [Strategy for Virus Resistance]", p. 3, Hideki Takahashi, "Uirusu-ni-tai-suru-Syukusyu-Teikosei [Host Resistance to Virus]").

Plant viruses multiply via successive infection steps, such as genome replication in individual cells, cell-to-cell movement through plasmodesmata, and long-distance movement through sieve tubes (Carrington et al., (1996) Plant Cell 8, 1669–1681; Baker et al., (1997) Science 276, 726–733). In these stages, the viral movement is facilitated by one or more virus-encoded proteins, called movement proteins (MPs) (Deom et al. (1992) Cell 69, 221–224). These should interact with various host factors (Carrington et al., supra; Baker et al., supra). Functional domains have been characterized in the MPs of a number of plant viruses. These include tobacco mosaic virus (TMV) and cucumber mosaic virus (CMV). In TMV, two RNA binding domains have been identified in the C terminal half of the MP (Citovsky et al., (1990) Cell 60, 637–647), while only one such domain was found in the C terminal third of the CMV MP (3a protein; Vaquero et al., (1997) J. Gen. Virol. 78, 2095–2099). Taking advantage of such RNA binding ability, viruses are thought to move from cell to cell as nucleoprotein complexes (Lazarowitz and Beachy, (1999) Plant Cell 11, 535–548). MPs from different virus families form a tubular structure (van Lent et al., (1991) J. Gen. Virol. 72, 2615–2623; Storms et al., (1995) Virology 214, 485–493; Huang et al., (2000) Virology 271, 58–64); and increase the size exclusion limit of plasmodesmata (Wolf et al., (1989) Science 246, 377–379). MPs were found in association with various subcellular structures, including endoplasmic reticulum, cytoskeleton, and plasmodesmata (Tomenius et al., (1987) Virology 160, 363–371; Atkins et al., (1991) J. Gen. Virol. 72, 209–211; Heinlein et al. (1995) Science 270, 1983–1985; McLean et al., (1995) Plant Cell 7, 2101–2114; Reichel et al., (1999) Trends Plant Sci. 4, 458–463).

In recent years, host factors that interact with viral MPs have become of interest. In the tomato, Tm-2 and Tm-$2^2$ are reported as resistance genes to tomato mosaic virus (ToMV) (Hall, (1980). Euphytica 29, 189–197; Fraser (1990) Annu. Rev. Phytopathol. 28, 179–200. 25). Mutant virus strains, overcoming the Tm-2 or Tm-$2^2$ phenotype, have amino acid substitutions in the MP. This suggests an interaction between MP and the resistance gene products (Meshi et al., (1989) Plant Cell 1, 515–522; Weber et al., (1993) J. Virol. 67, 6432–6438). Two homologous proteins in the *Nicotiana tabacum* and *Arabidopsis thaliana* Dna J family were identified in a yeast two-hybrid screen to interact with tomato spotted wilt virus (TSWV) MP (Soellick et al., (2000) Proc. Natl. Acad. Sci. USA 97, 2373–2378). Pectin methylesterase, localized at plasmodesmata, was found to interact with TMV MP. This suggests that this enzyme guides the MP and/or MP/RNA complex to plasmodesmata (Dorokhov et al., (1999) FEBS Lett. 461, 223–228; Chen et al., (2000) EMBO J. 19, 913–920). The CMV 2b protein, required for long-distance viral movement (Ding et al., (1995) EMBO J. 14, 5762–5772), was reported to interact with a tobacco protein that was very similar to a prokaryotic protein LytB, which is involved in penicillin tolerance in bacteria (Ham et al., (1999) Mol. Cells 9,548–555). Brigneti et al. (1998) EMBO J 17 6739–6746 proposed that CMV 2b functions as a suppressor of posttranscriptional gene silencing in host plants. Recently, Voinnet et al., (2000) Cell 103, 157–167 reported that potato virus XMP prevents the spread of the gene silencing signal in *N. benthamiana*.

Thus, there are a number of findings on plant viral MPs. Nevertheless, there has been no report relating to prevention of plant viral infection and conferring virus resistance to plants.

DISCLOSURE OF THE INVENTION

The present inventors found that by causing a protein capable of binding to a movement protein of a plant virus, which was identified by the present inventors, to be expressed in plants, the plant viral movement protein is prevented from intracting with a protein of plant hosts for viral infection, thereby blocking cell-to-cell movement of the plant virus and thus conferring resistance to the plant virus to the host plants. Thus, the present invention was completed.

According to an aspect, the present invention relates to a method for conferring resistance to a plant virus to plants. The method comprises the step of introducing into cells of the plant a polynucleotide encoding a protein capable of binding to a movement protein of the plant virus.

In one embodiment, the protein encoded by the polynucleotide contains a sequence indicated by position 1 to 86 of SEQ ID NO. 2, or contains the sequence having one or several amino acid substitutions, deletions, and/or additions, and binds to the movement protein of the plant virus.

In another embodiment, the polynucleotide contains a nucleotide sequence indicated by position 14 to 271 of SEQ ID NO. 1 or a nucleotide sequence hybridizable to said nucleotide sequence under stringent conditions.

In one embodiment, the plant virus is *Tobamovirus*, and preferably tomato mosaic virus (ToMV).

In one embodiment, the polynucleotide is derived from *Brassica campestris* or *Arabidopsis thaliana*.

According to another aspect, a plant produced by the method of the present invention is also provided.

In one embodiment, the plant is a monocotyledonous plant or a dicotyledonous plant. In one embodiment, the plant is tobacco.

BRIEF DESCRIPTION OF THE DRAWINGS

FIG. 1 shows electrophoresis photographs showing binding of ToMV MP to MIP102. (A) *E. coli* having the pGEX-Bc2 plasmid was grown without IPTG (lane 1) or with IPTG. The total proteins extracted from the bacteria were electrophoresed in 10% SDS-polyacrylamide gel and stained by CBB. (B) MP binding was assayed on a renatured protein blot. Proteins resolved as (A) were assayed on PVDF membrane and probed with $^{32}P$-labeled GST-PKA-MP. (C) Affinity-purified GST-MIP102 (lane 1) and GST (lane 2) were electrophoresed in 10% gel and stained. (D) Proteins resolved as (C) were blotted on PVDF membrane and assayed with $^{32}P$-labeled GST-PKA-MP as (B). Arrows show the positions of GST-MIP102 and GST. Positions of molecular mass (kDa) markers are shown on the left.

FIG. 2 is a diagram showing a nucleotide sequence of MIP102 cDNA (SEQ ID NO:1) and its putative amino acid sequence (SEQ ID NO:2). The underlined amino acid sequence indicates a putative single-stranded DNA binding domain, which is used for alignment in FIG. 3. The unique HindIII and EcoRI sites used for Southern blotting analysis are identified by double underlines. Arrows 1 and 2 indicate the positions of introns revealed by genomic DNA analysis.

FIG. 3 is a diagram showing multiple sequence alignment of MIP102 (SEQ ID NO:2) and AtKELP (SEQ ID NO:25) and similar sequences in the GenBank database. The upper alignment indicates comparison of a putative amino acid sequence of MIP102 and KELP (AtKELP) of *A. thaliana*. ★ indicates matched amino acid residues between MIP102 and dAtKELP. The lower alignment indicates comparison of various proteins in a putative single-stranded binding domain. MIP102 (SEQ ID NO:26), AtKELP (SEQ ID NO:27) and KIWI (SEQ ID NO:28) were aligned with homologous sequences identified in other organisms, such as human (PC4/p15, SEQ ID NO:31) (Ge and Roeder, 1994; Kretzschmar et al., (1994) Cell 78, 525–534), *C. elegans* (T13F2.2 protein, GenBank gene number Z81122, SEQ ID NO:30), and *S. pombe* (CAB10003.1 protein, GenBank gene number Z97185-2. SEQ ID NO:29).

FIG. 4 is an electrophoresis photograph showing genomic Southern hybridization of MIP102. *B. campestris* genomic DNA was digested with HindIII (lane 1), EcoRI (lane 2) or EcoRV (lane 3), fractioned through 1.0% agarose gel, and transferred to a nylon membrane. This blot was hybridized with $^{32}P$-labeled 440-bp PstI-HindIII fragment of pGEX-Bc2 (containing nucleotide 1 to 428 of the cDNA insert shown in FIG. 2). Positions of size (kb) markers are shown on the left.

FIG. 5 shows electrophoresis photographs showing binding of ToMV MP to the N terminus of MIP102. (A) Affinity-purified GST-MIP102 (lane 1), GST-MIP102dN (lane 2), GST-MIP102dC (lane 3) and GST (lane 4) were resolved in 10% SDS-polyacrylamide gel and blotted onto a PVDF membrane. After renaturation of the proteins, the blot was probed with $^{32}P$-labeled PKA-MP. (B) Protein profile in the gel used in (A) was revealed by CBB staining. Arrows show the positions of recombinant proteins. Broken arrows indicate the occurrence of protein degradation. Positions of molecular mass (kDa) markers are shown on the left.

FIG. 6 shows photographs showing green fluorescence of plant cells due to a reporter protein for viral cell-to-cell movement. (A) If the virus genome moves to neighboring cells, a green fluorescence protein is produced in the cells which in turn emit green light (the photograph designated "Multiple Cells"). (B) In contrast, if the virus does not perform cell-to-cell movement, fluorescence is generated only in a single cell (the photograph designated "One Cell").

FIG. 7 is a graph showing the influence of co-introduction of pART7-Bc2dC-HA and piL.G3on cell-to-cell movement. In FIG. 7, the vertical axis indicates the rate of cell-to-cell movement represented by the fluorescence spot ratio (multiple cells/total number), while the horizontal axis indicates the molar ratio of plasmids (pART7-Bc2dC-HA/piL.G3).

FIG. 8 is a graph showing the influence of co-introduction of pART7-Bc2dC-HA and piL.erG3 (ER localized GFP expression plasmid) on cell-to-cell movement. In FIG. 8, the vertical axis indicates the rate of cell-to-cell movement represented by the fluorescence spot ratio (multiple cells/total number), while the horizontal axis indicates the molar ratio of plasmids (pART7-Bc2dC-HA/piL.erG3).

FIG. 9 is a construction diagram showing the expression plasmid pART27-Bc2-HA.a which produces an N-terminal binding region of MIP102.

FIG. 10 shows electrophoresis photographs showing expression of a protein of interest in transformed tobacco. From the right in the following order, (A) Coomassie Brilliant Blue (CBB)-stained gel, (B) the result of use of HA tag antibodies (middle), and (C) the result of use of KELP antibodies. Of lanes in each result, the leftmost lane indicates a molecular mass marker and remaining lanes indicate transformed tobacco strains 101, 102, 105 and 118 from left in this order. The rightmost lane indicates a non-transformed tobacco (control).

Figure 11:
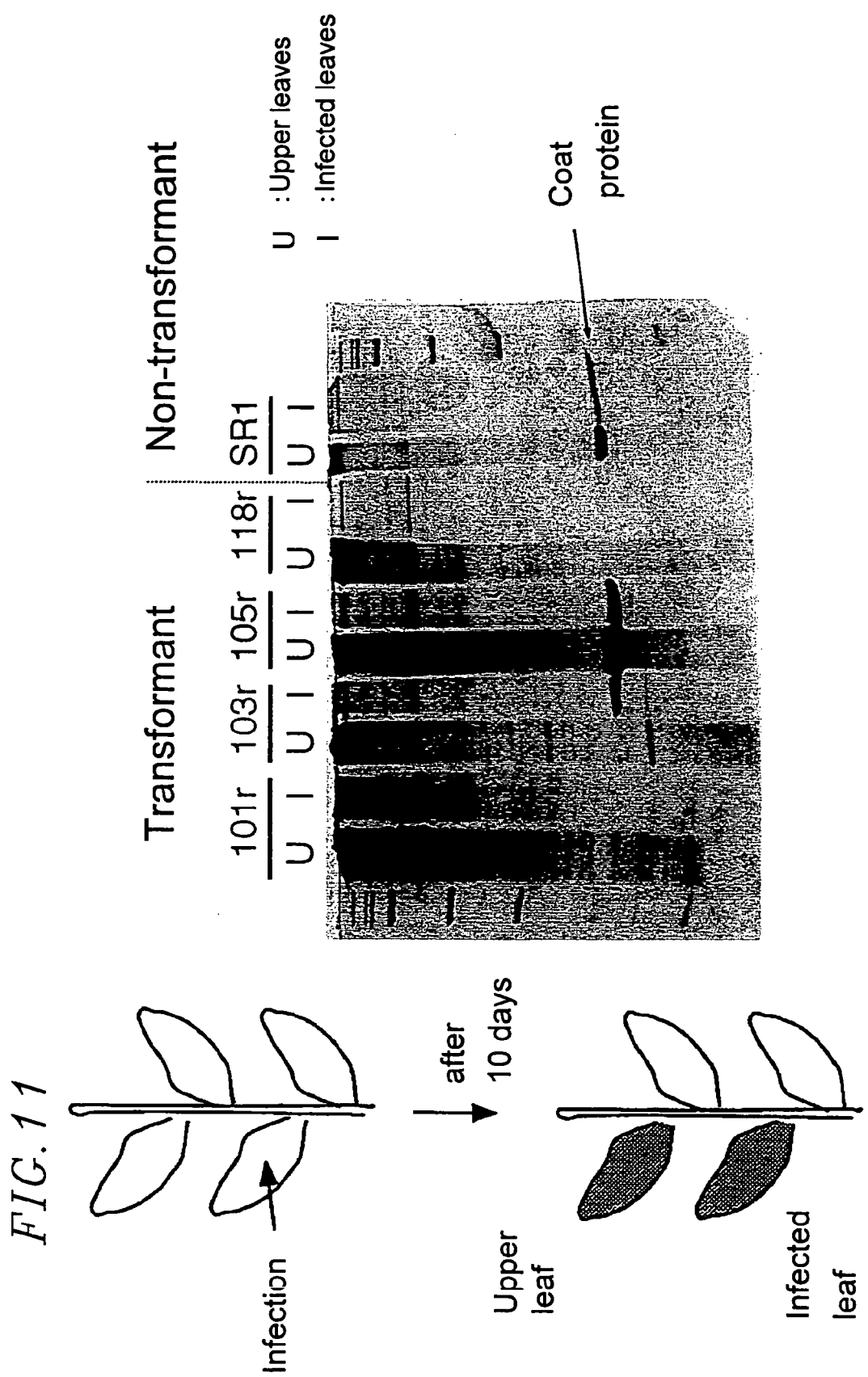

FIG. 11 shows an electrophoresis photograph showing the result of investigation of virus resistance due to ToMV particle infection. The opposite end lanes indicate molecular mass markers, and the remaining lanes indicate transformed tobacco strains 101r, 102r, 105r and 118r (these were regenerates from transformed tobacco strains 101, 102, 105 and 118), and a non-transformed tobacco (SR1) from left in this order. For each strain, the left lane indicates upper leaves (U) while the right lane indicates infected leaves (I). A band indicated by an arrow corresponds to coat protein.

Figure 12:
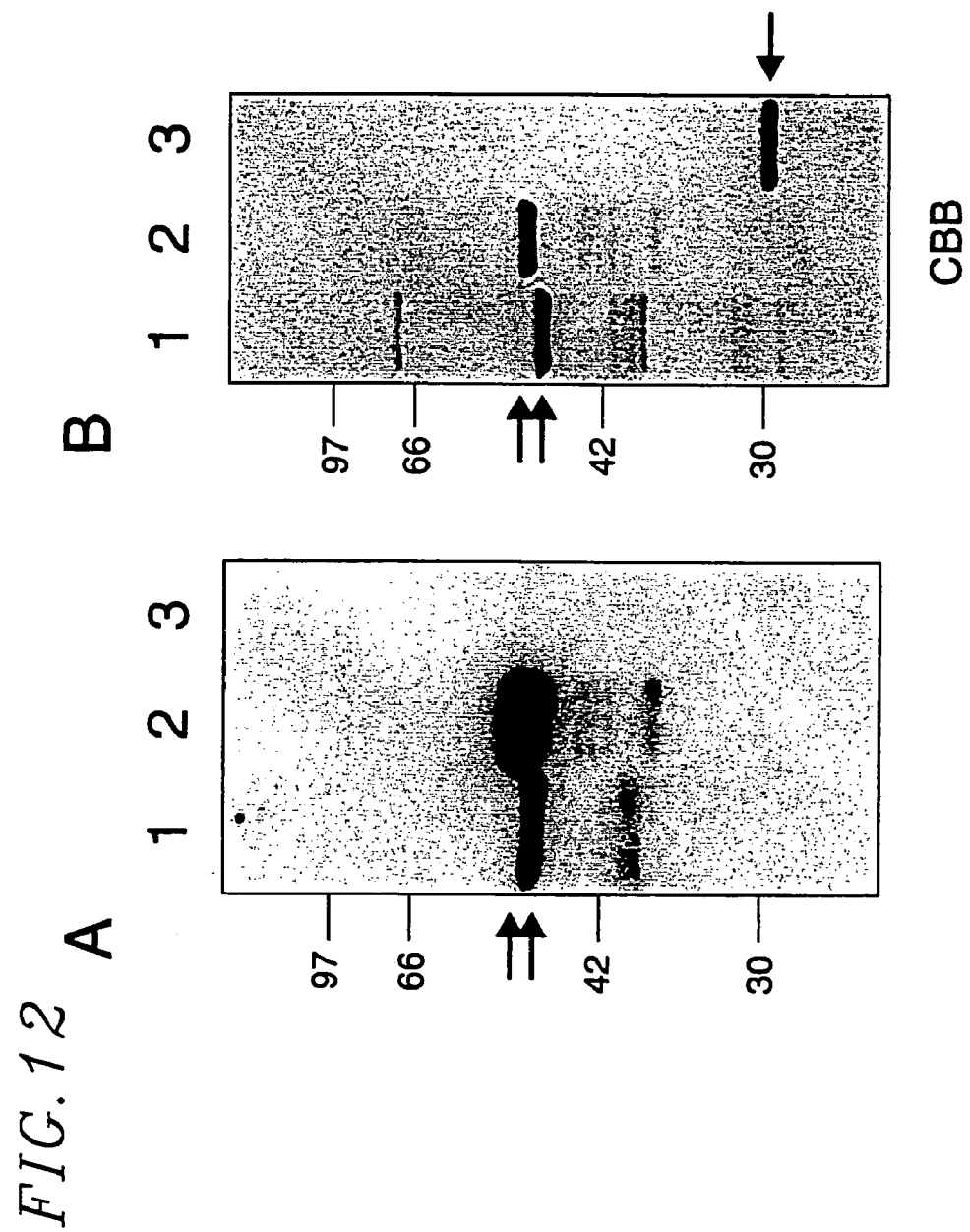

FIG. 12 shows electrophoresis photographs showing binding of ToMV MP to AtKELP. (A) Affinity-purified GST-AtKELP (lane 1), GST-MIP102 (lane 2), and GST (lane 3) were resolved in 10% SDS-polyacrylamide gel and blotted onto a PVDF membrane. After renaturation of the proteins, the blot was probed with $^{32}$P-labeled PKA-MP. (B) Protein profile in the gel used in (A) was revealed by CBB staining. Arrows show the positions of recombinant proteins. The size of GST-MIP102 was larger than GST-AtKELP due to extra 15 amino acids between GST and MIP102. Positions of molecular mass (kDa) markers are shown on the left.

Figure 13:
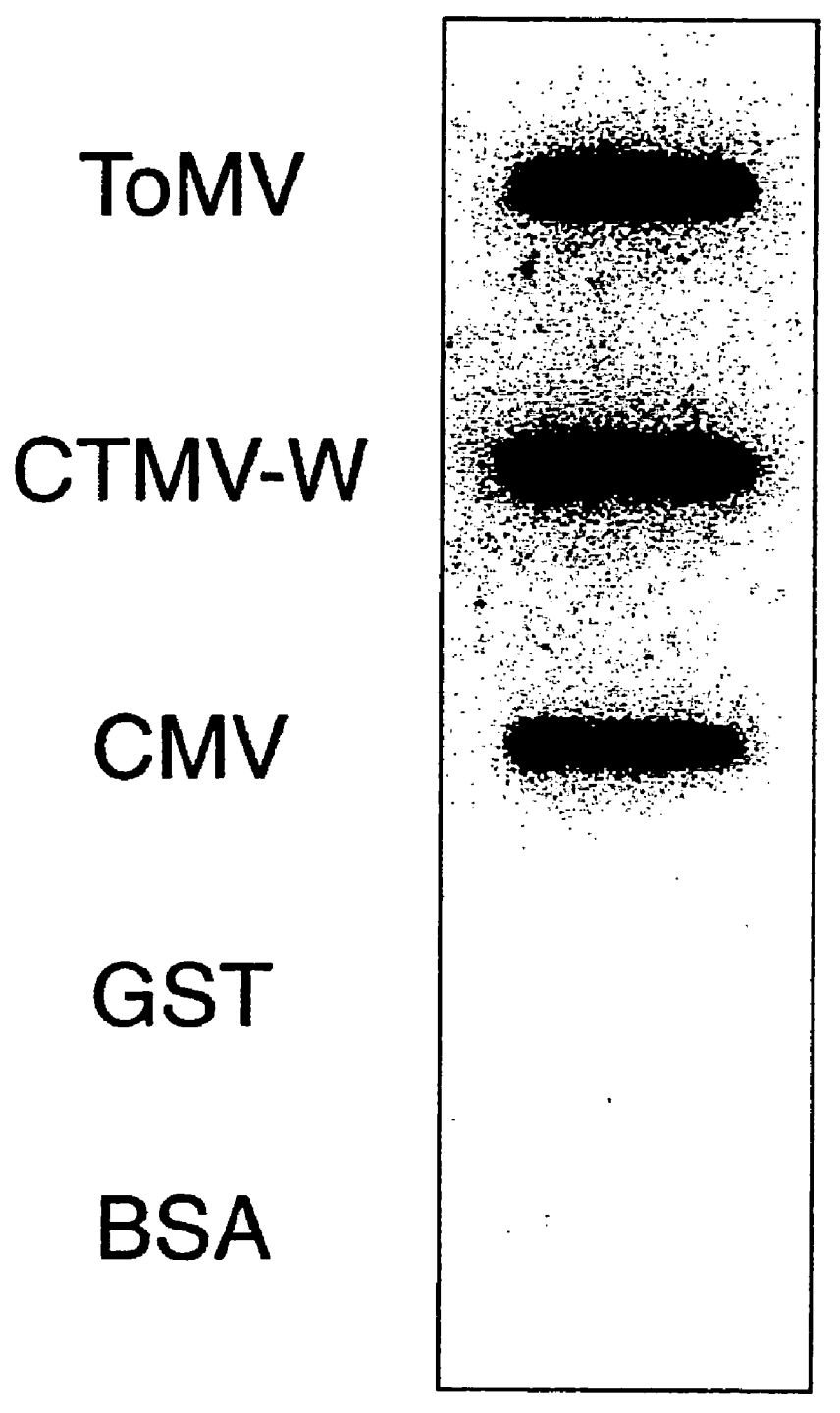

FIG. 13 is an electrophoresis photograph showing binding of AtKELP to MPs of various viruses. Equal amount (1 μg) of affinity-purified GST-MP (ToMV), GST-CTMVMP (CTMV-W), GST-CMVMP (CMV), GST and bovine serum albumin were immobilized onto a nitrocellulose membrane and probed with $^{32}$P-labeled PKA-AtKELP.

BEST MODE FOR CARRYING OUT THE INVENTION

According to the present invention, a method for conferring plant virus resistance to plants is provided. By "conferring plant virus resistance to plants" is intended that even if a plant is infected with a virus, disease damage is prevented or minimized. The method of the present invention comprises the step of introducing a polynucleotide encoding a protein capable of binding to a plant viral movement protein into plant cells.

A protein encoded by a polynucleotide used in the method of the present invention binds to a movement protein (MP) of an infecting plant virus. This interaction blocks the interaction the infecting viral movement protein and factors existing in a host plant, which may be involved in viral movement. Therefore, viral movement from cell to cell via plasmodesmata may be blocked. When the above-described protein is expressed in plants, plant viral cell-to-cell movement, and thus, tissue-to-tissue movement (long-distance movement) may be blocked. As a result, viral disease damage is prevented or minimized. Therefore, the polynucleotide used in the method of the present invention expresses a protein capable of binding a plant viral movement protein in plants, thereby conferring plant virus resistance to the plants.

The polynucleotide used in the method of the present invention may be screened for from a plant cDNA library as a polynucleotide encoding a protein capable of binding to a movement protein (MP) encoded in a plant viral RNA genome. Hereinafter, a protein capable of binding to this movement protein is referred to as a movement protein interacting protein (MIP). Movement protein interacting protein (MIPs) may be identified by a west western method which can search for an unknown protein capable of binding to a known protein. For example, a polynucleotide encoding a protein capable of binding to a movement protein (MP) encoded in the RNA genome of tomato mosaic virus (ToMV) may be screened for from a cDNA library of a plant, such as *Nicotiana tabacum, Arabidopsis thaliana*, and *Brassica campestris*. Such a MIP includes, but is not limited to, for example, MIP204 derived from a *N. tabacum* library, and MIP102, MIP105 and MIP106 derived from a *B. campestris* library. Among these MIPs, MIP102 may exhibit the highest binding to a tomato mosaic viral movement protein. The amino acid sequence of MIP102 and a nucleotide sequence encoding the same are indicated by SEQ ID NO. 2 and SEQ ID NO. 1.

The exemplary movement protein interacting protein MIP102 binds to a movement protein via the full length and a N terminal portion of MIP102. Therefore, in one embodiment, the polynucleotide of the method of the present invention encodes a protein containing an amino acid sequence from methionine (Met) at position 1 to glycine (Gly) at position 86 of SEQ ID NO. 2 in the sequence listing. In another embodiment, the polynucleotide used in the method of the present invention encodes a protein containing an amino acid sequence from methionine (Met) at position 1 to valine (Val) at position 165 of SEQ ID NO. 2 in the sequence listing. The polynucleotide used in the method of the present invention encodes a protein containing an amino acid sequence having one or more amino acid deletions, substitutions, and/or additions as long as the protein encoded by the polynucleotide has a function of binding to a viral movement protein.

In one embodiment, the polynucleotide of the present invention includes a polynucleotide having a nucleotide sequence of position 14 to 271 of SEQ ID NO. 1 in the sequence listing. In one embodiment, the polynucleotide of the present invention includes a polynucleotide having a nucleotide sequence of position 14 to 508 of SEQ ID NO. 1 in the sequence listing.

Nucleotide sequences disclosed herein as well as fragments and variants of proteins encoded by these sequences are encompassed by the present invention. By "fragment" is intended a portion of a nucleotide sequence, a portion of an amino acid sequence, and a protein encoded by the sequence. A fragment of a nucleotide sequence may encode a protein fragment keeping one or more functional biological activities of a native protein. In the method of the present invention, a disclosed nucleotide sequence and a fragment of a protein encoded by the sequence may also be used as long as they bind to a viral movement protein.

A variant of a protein encoded by the polynucleotide of the present invention means a protein derived from a native protein by one or more amino acid deletions (so-called shortening) or additions at the N terminus and/or the C terminus of the protein; an amino acid deletion or addition at one or more sites in the protein; or an amino acid substitution at one or more sites in the protein. Such a variant may be generated by, for example, polymorphism or artificial manipulation.

A protein encoded by the polynucleotide of the present invention may be modified by various methods (including amino acid substitution, deletion, shortening, and insertion). Methods for such manipulation are generally known in the art. For example, amino acid sequence variants of a protein encoded by a plant gene capable of regulating stress resistance according to the present invention may be prepared by mutations in DNA. Methods for mutagenesis and nucleotide sequence alterations are well known in the art. For example, see Kunkel (1985) Proc. Natl. Acad. Sci. USA 82:488–492; Kunkel et al. (1987) Methods in Enzymol. 154:367–382; U.S. Pat. No. 4,873,192; Walker and Gaastra, editors, (1983) Techniques in Molecular Biology (MacMillian Publishing Company, New York) and the references cited therein. Guidance as to appropriate amino acid substitutions that do not affect biological activity of the protein of interest may be found in the model of Dayhoff et al. (1987) Atlas of Protein Sequence and Structure (Natl. Biomed. Res. Found. Washington, D.C., herein incorporated by reference). Conservative substitutions, such as exchanging one amino acid with another having similar properties, may be preferred. Examples of conservative substitutions include, but are not limited to substitutions between hydrophobic amino acids (Ala, Ile, Leu, Met, Phe, Pro, Trp, Tyr, Val); hydrophilic amino acids (Arg, Asp, Asn, Cys, Glu, Gln, Gly, His, Lys, Ser, Thr); amino acids having aliphatic side chains (Gly, Ala, Val, Leu, Ile, Pro); amino acids having hydroxyl group containing side chains (Ser, Thr, Tyr); amino acids having sulfur atom containing side chains (Cys, Met); amino acids having carboxylic acid and amide containing side chains (Asp, Asn, Glu, Gln); amino acids having base containing side chains (Arg, Lys, His); amino acids having aromatic containing side chains (His, Phe, Tyr, Trp).

Therefore, "have one or more deletions, substitutions and/or additions" means that a number of amino acids which may be substituted, deleted and/or added by polymorphism or artificial manipulation (including well known methods described above) may be substituted, deleted and/or added. "Have one or more deletions, substitutions and/or additions" also means that any number of amino acids may be deleted, added, and/or substituted in the above-described amino acid sequence as long as the function of a protein encoded by the polynucleotide of the present invention can be expressed. It will be clearly appreciated by those skilled in the art that influences of alterations, such as amino acid substitutions, deletions and/or additions, on activity depend on positions, degrees, types, and the like of amino acids to be altered. A protein encoded by the polynucleotide of the present invention may have a number of deletions, substitutions and/or additions in the above-described amino acid sequence, which number satisfies the following amino acid sequence identity, as long as the function of the protein of the polynucleotide of the present invention is expressed.

The polynucleotide used in the method of the present invention includes a polynucleotide having a nucleotide sequence encoding a protein having an amino acid sequence, which has at least 70%, preferably at least 75%, more preferably at least 80%, even more preferably at least 90%, still even more preferably at least 95%, and most preferably at least 99% sequence identity with the amino acid sequence from Met at position 1 to Gly at position 86 of SEQ ID NO. 2 in the sequence listing, such that a protein encoded by this polynucleotide may bind to a viral movement protein. The polynucleotide used in the method of the present invention includes a polynucleotide having a nucleotide sequence encoding a protein having an amino acid sequence, which has at least 70%, preferably at least 75%, more preferably at least 80%, even more preferably at least 90%, still even more preferably at least 95%, and most preferably at least 99% sequence identity with the amino acid sequence from Met at position 1 to Val at position 165 of SEQ ID NO. 2 in the sequence listing, such that a protein encoded by this polynucleotide may bind to a viral movement protein.

The polynucleotide used in the method of the present invention includes a polynucleotide having a nucleotide sequence, which has at least 75%, preferably at least 80%, more preferably at least 85%, even more preferably at least 90%, still even more preferably at least 95%, and most preferably at least 99% sequence identity with a nucleotide sequence encoding the amino acid sequence from Met at position 1 to Gly at position 86 of SEQ ID NO. 2 in the sequence listing (preferably, a nucleotide sequence of A at position 14 to A at position 271 of SEQ ID NO. 1), such that a protein encoded by this polynucleotide may bind to a viral movement protein. The polynucleotide used in the method of the present invention includes a polynucleotide having a nucleotide sequence, which has at least 75%, preferably at least 80%, more preferably at least 85%, even more preferably at least 90%, still even more preferably at least 95%, and most preferably at least 99% sequence identity with a nucleotide sequence encoding the amino acid sequence from Met at position 1 to Gly at position 86 of SEQ ID NO. 2 in the sequence listing (preferably, a nucleotide sequence of A at position 14 to C at position 508 of SEQ ID NO. 1), such that a protein encoded by this polynucleotide may bind to a viral movement protein.

The polynucleotide of the present invention may contain an additional nucleotide sequence (e.g., a non-translated region) outside (i.e., at the 5' or 3' terminus of) a nucleotide sequence encoding a protein containing the amino acid sequence of the above-described region. Preferably, the polynucleotide used in the method of the present invention consists of a full length sequence of position 1 to 913 of SEQ ID NO. 1. The polynucleotide of the present invention includes all degenerate isomer of SEQ ID NO. 1. As used herein, the term "degenerate isomer" refers to DNA capable of encoding the same polypeptide where only degenerate codon(s) are different. For example, a DNA is called a degenerate isomer where a codon corresponding to an amino acid (e.g., codon AAC corresponding to Asn) with respect to the DNA having a base sequence of SEQ ID NO. 1 is replaced with its degenerate codon (e.g., codon AAT).

As used herein, "reference sequence" is a defined sequence used as a basis for sequence comparison. A reference sequence may be a subset or the entirety of a specified sequence; for example, as a segment of a full-length cDNA or polynucleotide sequence, or the complete cDNA or polynucleotide sequence.

As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those skilled in the art understand that to avoid a high similarity to a reference sequence due to inclusion of gaps in the polynucleotide sequence, a gap penalty is typically introduced and is subtracted from the number of matches.

Methods of alignment of sequences for comparison are well-known in the art. A preferred method for determining the best overall match between a reference sequence (the sequence of the present invention) and a subject sequence is a homology analysis utilizing BLAST (Altshul et al., 1997, Nucleic Acids Res., 25, 3389–3402). In sequence alignment, the reference sequence and the subject sequence are both DNA sequences. An RNA sequence may be compared by converting U's to T's. The result of said global sequence alignment is in percent identity. To calculate percent identity, DNA sequence alignment may be conducted using the default parameters of BLAST.

As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those skilled in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 80% sequence identity, preferably at least 85%, more preferably at least 90% and most preferably at least 95%, compared to a reference sequence using one of the alignment programs described using standard parameters. Those skilled in the art will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 70%, more preferably at least 75%, 80%, 90%, and most preferably at least 95%.

The terms "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman et al., J. Mol. Biol. 48:443 (1970). Thus, a peptide is substantially identical to a second peptide, for example, where the two peptides differ only by a conservative substitution. Peptides which are "substantially similar" share sequences as noted above except that residue positions which are not identical may differ by conservative amino acid changes. For peptide identity comparison, the GENE-TYX program may be used. In this case, the default parameters of the program may be used.

A polynucleotide fragment encoding a biologically active portion of a protein encoded by the polynucleotide used in the method of the present invention encodes at least 15, 25, 30, 50, 100, 125, 150, 175, 200 or 225 contiguous amino acids, or the total number of amino acids of the full length protein used in the method of the present invention (e.g., 243 amino acids in SEQ ID NO. 2). Generally, a fragment of a nucleotide sequence capable of conferring plant virus resistance to plants, which is used as a hybridization probe for a PCR primer does not necessarily encode a biologically active portion of a protein expressed by a polynucleotide capable of conferring plant virus resistance.

The exemplary movement protein interacting protein MIP102 is derived from *B. campestris*. The polynucleotide used in the method of the present invention may also include polynucleotides encoding movement protein interacting proteins derived from plants other than *B. campestris*. Such a polynucleotide may be isolated by, for example, conducting PCR using a primer designed based on the entirety or part of a disclosed nucleotide sequence and genomic DNA of a selected plant as a template, and thereafter, using the resultant amplified DNA fragment as a probe, screening a genomic DNA or cDNA library of the same plant. In this manner, methods such as PCR, hybridization, and the like may be used to identify such sequences based on the sequence identity to the sequence set forth herein. Sequences isolated based on their sequence identity to the entirety of the sequences set forth herein or fragments thereof, are encompassed by the present invention.

In a hybridization method, all or part of a known nucleotide sequence can be used as probes which hybridize selectively to other corresponding nucleotide sequences existing in a group of cloned genomic DNA fragments or cDNA fragments derived from a selected organism (i.e., a genome library or a cDNA library). These hybridization probes may be genomic DNA fragments, cDNA fragments, RNA fragments, or other oligonucleotides, and may be labeled with a detectable group such as $^{32}$P, or any other detectable marker. Preparation of probes for hybridization and construction of cDNA libraries and genomic libraries are generally known in the art and is disclosed in Sambrook et al. (1989) Molecular Cloning: A Laboratory Manual (2d ed., Cold Spring Harbor Laboratory Press, Plainview, N.Y.), herein incorporated by reference.

For example, the entirety or one or more portions of the nucleotide sequence of the plant gene capable of conferring plat virus resistance set forth herein may be used as probes capable of hybridizing specifically to the sequence of the plant gene capable of conferring virus resistance to plants and messenger RNA thereof. In order to achieve specific hybridization under various conditions, such probes are unique between the sequences of plant genes capable of conferring virus resistance to plants, and preferably contain a sequence of at least about 10 nucleotides in length, and most preferably at least about 20 nucleotides in length. Such probes may be used so as to PCR amplify the sequences of plant genes capable of conferring virus resistance to plants from selected organisms. Methods for PCR amplification are well known in the art (PCR Technology: Principles and Applications for DNA Amplification, H A Erlich ed., Freeman Press, New York, N.Y. (1992); PCR Protocols: A Guide to Methods and Applications, Innis, Gelfland, Snisky, and White, eds., Academic Press, San Diego, Calif. (1990); Mattila et al. (1991) Nucleic Acids Res. 19:4967; Eckert, K. A. and Kunkel, T. A. (1991) PCR Methods and Applications 1:17: PCR, McPherson, Quirkes, and Taylor, IRL Press, Oxford, herein incorporated by reference). This technique may be used as a diagnostic assay for isolating additional coding sequences from a desired organism or determining the presence of coding sequences in organisms. The hybridization technique includes hybridization screening of plated DNA libraries (either plaques or colonies e. g., see Sambrook et al. (1989) Molecular Cloning: A Laboratory Manual (2nd Ed., Cold Spring Harbor Laboratory Press, Plainview, N.Y.)).

Such sequence hybridization may be conducted under stringent conditions. The terms "stringent conditions" or "stringent hybridization conditions" includes reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe. Alternatively, stringency conditions can be adjusted to allow some mismatching in sequences so that lower degrees of similarity are detected. Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) and the temperature is at least about 30° C. for short probes (pH 7.0 to 8.3) (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization at 42° C. in solution containing 50% formamide, 4.4×SSC, 20 mM phosphate buffer (pH 6.8), 1× Denhardt's solution, 0.2% SDS and denatured salmon sperm DNA (0.1 mg/ml), a wash in 2×SSC containing 0.1% SDS at room temperature, and a final wash in 0.2×SSC containing 0.1% SDS at 42° C.

Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 138:267–284 (1984): Tm=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those skilled in the art will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) Laboratory Techniques in Biochemistry and Molecular Biology-Hybridization with Nucleic Acid Probes, Part I, Chapter 2 (Elsevier, New York): and Ausubel, et al., Eds. (1995), Current Protocols in Molecular Biology, Chapter 2 (Greene Publishing and Wiley-Interscience, New York). Also see Sambrook et al. (1989) Molecular Cloning: A Laboratory Manual (2d ed., Cold Spring Harbor Laboratory Press, Plainview, N.Y.) (these are herein incorporated by reference).

The base sequence of an obtained gene may be determined by a nucleotide sequence analysis method known in the art or a commercially available automatic sequencer.

The polynucleotide of the present invention may be typically obtained in accordance with a method set forth herein or may be obtained by chemical synthesis based on the sequence disclosed herein. For example, the polynucleotide of the present invention may be synthesized using a polynucleotide synthesizer (Applied BioSystems (at present, Perkin Elmer), following the manufacturer's instructions.

A polypeptide produced in accordance with a procedure, such as a genetic engineering technique or a chemically synthesizing technique, as described above may be confirmed to have desired activity, i.e., conferring virus resistance as follows. An expression vector containing the polynucleotide is produced. This expression vector is expressed in an appropriate cell to produce a protein. A procedure substantially identical to that described in Example 1 below may be used to determine that the protein binds to a plant viral movement protein (MP) of interest. Thereafter, an expression vector containing the polynucleotide is prepared. A procedure substantially identical to that described in Example 4 below may be used to confirm that when the protein is introduced into plant cells together with viruses, the protein suppresses cell-to-cell movement of the viruses where a reporter gene, such as a green fluorescence gene, is used as an indicator.

The polynucleotide used in the method of the present invention confers plant virus resistance to plants. Plant viruses are not necessarily specific. A movement protein interacting protein capable of binding to a movement protein of a certain virus may bind to a movement protein of another virus. For example, MIP102 and AtKELP (a protein having about 75% amino acid sequence identity to the full length of MIP102), which are typical proteins capable of binding to a tomato mosaic viral movement protein, also may bind to Brassicaceae mosaic virus (*crucifer tobamovirus*) and cucumber mosaic virus.

In Examples set forth herein, virus resistance to tomato mosaic virus (ToMV) is shown for purposes of illustration. The method of the present invention may also confer resistance to other plant viruses to plants. Examples of plant viruses, for which resistance is sought, include, but are not limited to, viruses of the genera *Tobamovirus, Tobravirus, Dianthovirus, Alfamovirus, Bromovirus, Cucumovirus, Comovirus, Nepovirus, Caulimovirus, Geminivirus, Potivirus,* and *Tospovirus*. The polynucleotide used in the method of the present invention may be obtained by identifying a plant viral movement protein of a plant which is to be conferred resistance, and screening for a protein capable of binding to the identified movement protein by a west western screening method as described in Example 1.

The polynucleotide of the present invention may be linked to an appropriate plant expression vector using a method well known to those skilled in the art, and introducing the vector into a plant cell by a known recombinant technique. The introduced gene is incorporated in DNA in the plant cell. Note that the DNA in the plant cell includes chromosomes as well as DNA contained in various organelles in the plant cell (e.g., mitochondrion, chloroplast, and the like).

As used herein, a "plant expression vector" refers to a nucleic acid sequence to which various regulatory elements, such as a promoter which regulates expression of a gene of the present invention, are operatively linked in host plant cells. The term "control sequence" as used herein refers to a DNA sequence having a functional promoter and any related transcription element (e.g., an enhancer, a CCAAT box, a TATA box, and a SPI site). The term "operatively linked" as used herein indicates that a polynucleotide is linked to a regulatory element which regulates expression of a gene, such as a promoter or an enhancer such that the gene can be expressed. Plant expression vectors may preferably include plant gene promoters, terminators, drug-resistance genes, and enhancers. It is well known to those skilled in the art that the type of an expression vector and the type of a regulatory element used may be changed depending on the host cell. Plant expression vectors used in the present invention may have a T-DNA region. The T-DNA region can enhance the efficiency of gene introduction, particularly when *Agrobacterium* is used to transform a plant.

The term "plant gene promoter" as used herein refers to a promoter which is expressed in plants. A plant promoter fragment can be employed which will direct expression of the polynucleotide of the present invention in all tissues of regenerated plants. Examples of a promoter for structural expression include a promoter for nopaline synthase gene (Langridge, 1985, Plant Cell Rep. 4, 355), a promoter for producing cauliflower mosaic virus 19S—RNA (Guilley, 1982, Cell 30, 763), a promoter for producing cauliflower mosaic virus 35S-RNA (Odell, 1985, Nature 313, 810), a rice actin promoter (Zhang, 1991, Plant Cell 3,1155), a maize ubiquitin promoter (Cornejo 1993, Plant Mol. Biol. 23, 567), and the REXφ promoter (Mitsuhara, 1996, Plant Cell Physiol. 37, 49).

Alternatively, plant promoters can direct expression of the polynucleotide of the present invention in a specific tissue or may be otherwise under more precise environmental or developmental control. Such promoters are herein referred to as "inducible" promoters. Examples of inducible promoters include promoters which are inducible by environmental conditions, such as infection or invasion of pathogens, injury of plants, light, low temperature, high temperature, dryness, ultraviolet irradiation, spray of a specific compound, or the like. Examples of such promoters include a promoter for a gene encoding ribulose-1,5-diphosphate carboxylase small subunit which is induced by light irradiation (Fluhr, 1986, Proc. Natl. Acad. Sci. USA 83, 2358), a promoter for the rice chitinase gene expressed due to infection or invasion of molds, bacteria, or viruses (Xu, 1996, Plant Mol. Biol. 30, 387), a promoter for the tobacco PR protein gene (Ohsima, 1990, Plant Cell 2, 95), a promoter for the rice lip19 gene inducible by low temperature (Aguan, 1993, Mol. Gen. Genet. 240, 1), promoters for rice hsp72 and hsp80genes inducible by high temperature (Van Breusegem, 1994, Planta 193, 57), a promoter for the rab16 gene of *Arabidopsis thaliana* inducible by dryness (Nundy, 1990, Proc. Natl. Acad. Sci. USA 87, 1406), and a promoter for the maize alcohol dehydrogenase gene inducible by ultraviolet irradiation (Schulze-Lefert, 1989, EMBO J. 8, 651). A promoter for the rab16 gene is inducible by spraying abscisic acid which is a plant hormone.

A "terminator" is a sequence which is located downstream of a region encoding a protein of a gene and which is involved in the termination of transcription when DNA is transcribed into mRNA, and the addition of a poly A sequence. It is known that terminators contribute to the stability of mRNA, and have an influence on the level of gene expression. Examples of such terminators include, but are not limited to, a CaMV35S terminator and a terminator for the nopaline synthetase gene (Tnos).

A "drug-resistant gene" is desirably one that facilitates screening of transformed plants. The neomycin phosphotransferase II (NPTII) gene for conferring kanamycin resistance, the hygromycin phosphotransferase gene for conferring hygromycin resistance, and the like may be preferably used. The present invention is not so limited.

An "enhancer" may be used so as to enhance the expression efficiency of a gene of interest. As such an enhancer, an enhancer region containing an upstream sequence within the CaMV35S promoter is preferable. A plurality of enhancers may be used for each plant expression vector.

If polypeptide expression is desired, it is generally desirable to include a polyadenylation region at the 3' terminus of a polynucleotide coding region. The polyadenylation region can be derived from the natural gene, from a variety of other plant genes, or from T-DNA. The 3' terminus sequence to be added can be derived from, for example, the nopaline synthase or octopine synthase genes, or alternatively from another plant gene, or less preferably from any other eukaryotic gene.

Plant expression vectors as described above may be prepared using a gene recombination technique well known to those skilled in the art. In construction of a plant expression vector, pBI vectors, pUC vectors, pART vectors, or the like are preferably used. The present invention is not so limited.

A plant material for DNA introduction can be appropriately selected from leaves, stems, roots, tubers, protoplasts, calluses, pollen, embryos, shoot primordia, an the like according to the introduction method or the like. A "plant cell" may be any plant cell. Examples of a "plant cell" include cells of tissues in plant organs, such as leaves and roots; calluses; and suspension culture cells. The plant cell may be in any form of a culture cell, a culture tissue, a culture organ, or a plant. Preferably, the plant cell is a culture cell, a culture tissue, or a culture organ. More preferably, the plant cell is a culture cell.

A plant culture cell, to which DNA is introduced, is generally a protoplast. DNA is introduced to a plant culture cell by a physical/chemical method, such as an electroporation method, a polyethylene glycol method, or the like. A plant tissue, to which DNA is introduced, is a leaf, a stem, a root, a tuber, a callus, pollen, an embryo, a shoot primordium, preferably a leaf, a stem, and a callus. DNA is introduced into a plant tissue by a biological method using avirus or *Agrobacterium*, or a physical/chemical method, such as a particle gun method, or the like. The method using *Agrobacterium* is disclosed, for example, in Nagel et al. (Microbiol. Lett., 67, 325 (1990)). In this method, a plant expression vector is first used to transform *Agrobacterium* (e.g., by electroporation), and then the transformed *Agrobacterium* is introduced into a plant tissue by a well-known method, such as a leaf disc method. A particle gun method is described in, for example, Klein et al. (1987), Nature 327:70–73; and Christon, P. Plant J. (1992) 2,275–281. A protocol for transformation and a protocol for introduction of a nucleotide sequence into plants vary depending on a target plant to be transformed or the type of a plant cell (i.e., monocotyledon or dicotyledon). Examples of an appropriate method for introducing a nucleotide sequence into plant cells and subsequently inserting the sequence into the plant genome include microinjection (Crossway et al. (1986) Biotechniques 4:320–334), electroporation (Riggs et al. (1986) Proc. Natl. Acad. Sci. USA 83:5602–5606), *Agrobacterium* mediated transformation (Townsend et al., U.S. Pat. No. 5,563,055), direct gene transfection (Paszkowski et al. (1984) EMBO J. 3:2717–2722), and ballistic particle acceleration (e.g., Sanford et al., U.S. Pat. No. 4,945,050; Tomesra, U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment", Plant Cell, Tissue, and Organ Culture: Fundamental Methods, Gamborg and Phillips ed., (Springer-Verlag, Berlin); and McCabe et al. (1988) Biotechnology 6:923–926). Also, see the following references: Weissinger et al. (1988) Ann. Rev. Genet. 22:421–477; Sanford et al. (1987) Particulate Science and Technology 5:27–37 (onion); Christou et al. (1988) Plant Physiol. 87:671–674 (soy bean); McCabe et al. (1988) Bio/Technology 6:923–926 (soy bean); Finer and McMullen (1991) In Vitro Cell Dev. Biol. 27P:175–182 (soybean); Singh et al. (1998) Theor. Appl. Genet. 96:319–324 (soy bean); Datta et al. (1990) Biotechnology 8:736–740 (rice); Klein et al. (1988) Proc. Natl. Acad. Sci. USA85:4305–4309 (maize); Klein et al. (1988) Biotechnology 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment", Plant Cell, Tissue, and Organ Culture: Fundamental Methods, Gamborg ed. (Springer-Verlag, Berlin) (maize); Klein et al. (1988) Plant Physiol. 91:440–444 (maize); Fromm et al. (1990) Biotechnology 8:833–839 (maize); Hooykaas-Van Slogteren et al. (1984) Nature (London) 311:763–764; Bowen et al., U.S. Pat. No. 5,736,369 (crop species); Bytebier et al. (1987) Proc. Natl. Acad. Sci. USA 84:5345–5349 (Liliaceae); De Wet et al. (1985) The Experimental Manipulation of Ovule Tissues, Chapmann et al. eds. (Longman, New York) pp. 197–209 (pollen); Kaeppler et al. (1990) Plant Cell Reports 9:415–418 and Kaeppler et al. (1992) Theor. Appl. Genet. 84:560–566 (whisker mediated transformation); D'Halluin et al. (1992) Plant Cell 4:1495–1505 (electroporation); Li et al. (1993) Plant Cell Reports 12:250–255, and Christou and Ford (1995) Annals of Botany 75:407–413 (rice); Osjoda et al. (1996) Nature Biotechnology 14:745–750 (maize (via *Agrobacterium tumefaciens*)) (all of these are herein incorporated by reference). These methods are well known in the art. A method suitable for a plant to be transformed can be appropriately selected.

A cell, into which a plant expression vector has been introduced, is selected for drug resistance, such as kanamycin resistance. The transformed cell can be regenerated to a plant by a commonly used method. See, for example, McCormick et al. (1986) Plant Cell Reports 5:81–84.

A plant cell, into which the polynucleotide of the present invention has been introduced, can be regenerated to a plant by culturing the plant cell in redifferentiation medium, hormone-free MS medium, or the like. A young rooted plant can be grown to a plant by transferring it to soil, followed by cultivation. Redifferentiation methods vary depending on the type of a plant cell. Redifferentiation methods for various plants are described: rice (Fujimura, 1995, Plant Tissue Culture Lett. 2, 74); maize (Shillito, 1989, Bio/Technol. 7, 581; Gorden-Kamm, 1990, Plant Cell 2, 603); potato (Visser, 1989, Theor. Appl. Genet. 78, 594); and tobacco (Nagata, 1971, Planta 99, 12).

Expression of an introduced gene of the present invention in a regenerated plant can be confirmed by a method well known to those skilled in the art. This confirmation may be carried out using, for example, Northern blotting analysis. Specifically, total RNA is extracted from a plant leaf, is subjected to electrophoresis on denaturing agarose, and is blotted to an appropriate membrane. This blot is subjected to hybridization with a labeled RNA probe complementary to a portion of the introduced gene, thereby detecting mRNA of a gene of the present invention. These plants may then be grown, and either pollinated with the same transformed strain or different strains, and the resulting hybrid having the desired phenotypic characteristic may be identified. Two or more generations may be grown to ensure that the subject phenotypic characteristic is stably maintained and inherited and then seeds harvested to ensure the desired phenotype or other property has been achieved.

Plants which can be generated by the method of the present invention include any plant to which a gene can be introduced. As used herein, the term "plant" includes reference to whole plants, plant organs (e.g., leaves, stems, roots, etc.), seeds, plant propagators (e.g., pollen), and plant cells, and progeny of same. Plant cells as used herein include, without limitation, seeds, suspension cultures, embryos, meristematic regions, callus tissue, leaves, roots, shoots, gametophytes, sporophytes, pollen, andmicrospores. The term "plant" includes monocotyledonous and dicotyledonous plants. Such plants include any useful plants, particularly crop plants, vegetable plants, and flowering plants of garden varieties. The most preferable plant to which the present invention is applied is tobacco.

Examples of types of plants that can be used in the present invention include plants in the families of Solanaceae, Poaceae, Brassicaceae, Rosaceae, Leguminosae, Cucurbitaceae, Lamiaceae, Liliaceae, Chenopodiaceae and Umbelliferae.

Examples of plants in the Solanaceae family include plants in the *Nicotiana, Solanum, Datura, Lycopersicon* and *Petunia* genera. Specific examples include tobacco, eggplant, potato, tomato, chili pepper, and petunia.

Examples of plants in the Poaceae family include plants in the *Oryza, Hordenum, Secale, Saccharum, Echinochloa* and *Zea* genera. Specific examples include rice, barley, rye, barnyard grass, sorghum, and maize.

Examples of plants in the Brassicaceae family include plants in the *Raphanus, Brassica, Arabidopsis, Wasabia*, and *Capsella* genera. Specific examples include Japanese white radish, rapeseed, *Arabidopsis thaliana*, Japanese horseradish, and shepherd's purse.

Examples of plants in the Rosaceae family include plants in the *Orunus, Malus, Pynus, Fragaria*, and *Rosa* genera. Specific examples include plum, peach, apple, pear, Dutch strawberry, and rose.

Examples of plants in the Leguminosae family include plants in the *Glycine, Vigna, Phaseolus, Pisum, Vicia, Arachis, Trifolium, Alfalfa*, and *Medicago* genera. Specific examples include soybean, adzuki bean, kidney bean, pea, fava bean, peanut, clover, and bur clover.

Examples of plants in the Curcurbitaceae family include plants in the *Luffa, Curcurbita*, and *Cucumis* genera. Specific examples include gourd, pumpkin, cucumber, and melon.

Examples of plants in the Lamiaceae family include plants in the *Lavandula, Mentha*, and *Perilla* genera. Specific examples include lavender, peppermint, and beefsteak plant.

Examples of plants in the Liliaceae family include plants in the *Allium, Lilium*, and *Tulipa* genera. Specific examples include onion, garlic, lily, and tulip.

Examples of plants in the Chenopodiaceae family include plants in the *Spinacia* genera. A specific example is spinach.

Examples of plants in the Umbelliferae family include plants in the *Angelica, Daucus, Cryptotaenia*, and *Apitum* genera. Specific examples include Japanese udo, carrot, honewort, and celery.

Virus resistance conferred by the method of the present invention may be inherited to the primary generation of transformed plants as well as subsequent generations of the plants. The virus resistance conferred by the peptide of the present invention may be exhibited in the primary generation of transformed plants and subsequent generations of the plants, propagators thereof (e.g., pollen), and seeds produced from the propagators. Inheritance of the polynucleotide used in the method of the present invention into subsequent generations may be confirmed by southern analysis using a sequence of the polynucleotide disclosed herein as a probe.

The nomenclature used hereafter and the laboratory procedures described hereafter often involve well known and commonly employed procedures in the art. Standard techniques are used for recombinant methods, polynucleotide synthesis, cell culture, transformation and plant regeneration. The techniques and procedures are generally performed according to conventional methods in the art and various general references (see, generally, Sambrook et al. Molecular Cloning: A Laboratory Manual, 2nd ed. (1989) Cold Spring Harbor Laboratory Press, Cold Spring Harbor, N.Y., which is incorporated herein by reference).

Hereinafter, the present invention will be described by way of examples. The present invention is not so limited. Materials, reagents, and the like used in the examples are available from commercial sources, unless otherwise mentioned.

EXAMPLES

Example 1

Far-Western ("West Western") Screening for Movement Protein Interacting Protein (MIP)

To identify plant proteins that bind to ToMV MP, the present inventors constructed *N. tabacum* and *B. campestris* expression cDNA libraries of λ GEX5. The construction of the cDNA libraries is the following. Leaves from *N. tabacum* cv. Samsun NN, stigma from *B. campestris* (S9/S9) and flower buds from *A. thaliana* ecotype Columbia were subjected to RNA isolation with QuickPrep Micro mRNA Purification Kit (Amersham Pharmacia Biotech), followed by cDNA synthesis with Timesaver cDNA Synthesis Kit (Amersham Pharmacia Biotech). A λ phage vector λGEX5 (Fukunaga et al., (1997) EMBO J. 16, 1921–1933; this vector has an IPTG inducible promoter and a cDNA-cloning site downstream of a GST reading frame) was used for construction of cDNA expression libraries. Phosphorylated oligonucleotide adapters (5'-AGGTGCTGG-3' SEQ ID NO:3, 5'-CCAGCACCTGCA-3' SEQ ID NO:4) were annealed and ligated to cDNAs to make compatible ends with the SfiI-cut vector. The cDNAs were ligated with the vector arms and subjected to in vitro packaging. The phage libraries were amplified in *E. coil* strain BB4.

Far-western screening for MP interacting protein (MIP) was carried out based on the protein-protein binding between each GST-fused cDNA product immobilized on a membrane and GST-fused ToMV MP (GST-PKA-MP) phosphorylated with [γ-$^{32}$P]ATP for probing.

GST-fused ToMV MP (GST-PKA-MP) phosphorylated with [γ-$^{32}$P]ATP was prepared as follows.

Initially, ToMV MP expression plasmid was prepared as follows. The plasmid pGEX-30K for the expression of glutathione-S-transferase (GST)-fused ToMV MP (GST-MP) was described previously (Matshushita et al., (2000) J. Gen. Virol. 81, 2095–2102). To add a consensus phosphorylation sequence for protein kinase A between GST and MP, synthetic oligonucleotides 30K-PKA1 (5'-AATTCGTCGT-GCATCTGTTGC-3' SEQ ID NO:5) and 30K-PKA2 (5'-AATTGCAACAGATGCACGACG-3' SEQ ID NO:6) coding for the five amino acids RRASV (SEQ ID NO:32) were annealed and inserted into the EcoRI site of pGEX-30K in the proper orientation to generate pGEX-PKA-30K. This plasmid was used for production of a recombinant protein GST-PKA-MP. The 1.1-kb EcoRI-NotI insert of pGEX-PKA-30K was placed between the EcoRI and NotI sites of the pGEX-6P-2 vector to construct pGEX-6P2-PKA-30K . This plasmid was used for production of GST-P-PKA-MP, which could be cleaved by PreScission Protease (Amersham Pharmacia Biotech) to remove GST and prepare a recombinant protein PKA-MP.

Construction of pGEX-30KdA and pGEX-30KdSX plasmids was described previously (Matsushita et al., supra). The recombinant protein GST-MPdA encoded by pGEX-30KdA had a deletion of the C-terminal 9 amino acids that were replaced by 27 artificial residues derived from the vector (QVALFGEMCAEPLFVYFSKYIQICIRS SEQ ID NO:7). Another recombinant protein, GST-MPdSX, encoded by pGEX-30KdSX had a deletion of the C-terminal 31 amino acids that were replaced by 7 residues derived from the vector (LERPHRD SEQ ID NO:8).

Production and purification of recombinant proteins were conducted as follows. Recombinant GST-fused proteins were produced in *E. coli* XL10-Gold (Stratagene) having appropriate plasmids and purified by using Glutathione Sepharose beads (Amersham Pharmacia Biotech) as described previously (Matsushita et al., supra). Anti-GST antibody (goat) purchased from Amersham Pharmacia Biotech was used to identify the fusion protein by western blotting analysis. Purified proteins were stored in NETN-D buffer (50 mM Tris-HCl, pH 8.0, 1 mM EDTA, 150 mM NaCl, 0.5% Nonidet P-40, 1 mM DTT).

$^{32}$P-labeled protein probes were prepared as follows. Glutathione Sepharose beads conjugated with about 1 μg of recombinant GST-fused protein were suspended in 200 μl of kinase buffer (50 mM Tris-HCl, 10 mMMgCl$_2$, pH8.5) containing 3.7 MBq of [λ-$^{32}$P]ATP (168 TBq/mmol) and 10 units of the catalytic subunit of protein kinase A (New England BioLabs). This reaction was continued for 30 min on a rotator at 30° C. and terminated by washing the beads 4 times with 1 ml of 50 mMTris-HCl (pH 8.0) buffer. The phosphorylated protein was eluted from beads with 50 mM Tris-HCl (pH 8.0) buffer containing 10 mM glutathione. Where indicated, the phosphorylated GST-fused protein was digested with PreScission Protease to remove GST domain before using as a probe for binding experiments. The specific radioactivity of the probe was about 1×10$^7$ cpm/μg protein.

Far-western screening of the cDNA library was conducted as follows. E. coli strain BB was used for infection with the phage library. The bacteria were incubated for 3 h at 42° C. to obtain plaques at a density of 100 to 200/cm². The bacterial plates were overlaid with nitrocellulose filters wetted with 10 mM IPTG and further incubated for 3.5 h at 37° C. The filters were washed and incubated in a blocking solution, Block Ace (Dainippon-Pharm co.), for 1 h at 4° C. before the incubation with $^{32}$P-labeled GST-PKA-MP ($2\times10^5$ cpm/ml) for 16 h at 4° C. The filters were then washed four times each for 5 min in PBS (137 mM NaCl, 2.68 mM KCl, 10.14 mM $Na_2HPO_4$, 1.76 mM $KH_2PO_4$, pH 7.4) supplemented with 0.2% Triton X-100 and subjected to autoradiography on BAS1500 system (Fuji Photo Film).

Several positive clones were isolated, such as MIP204 from the *N. tabacum* library, and MIP102, MIP105 and MIP106 from the *B. campestris* library. Among these positive clones, MIP102 exhibited the highest binding activity and was consequently selected for further analysis.

Phage DNA isolated from the MIP102 clone was used to reconstruct the expression plasmid pGEX-Bc2 producing GST-fused MIP102, which was used for protein-binding assay (FIG. 1).

Protein-protein interaction was examined by a binding assay between $^{32}$P-labeled protein probe and target protein that was immobilized on a membrane. The target proteins were separated by SDS-polyacrylamide gel electrophoresis and transferred onto PVDF membrane (Millipore). After washing with buffer A (50 mM Tris-HCl, 20% 2-propanol, pH 8.0) and buffer B (50 mM Tris-HCl, 5 mM β-mercaptoethanol, pH 8.0) each for 1 h at room temperature, the membrane was incubated for 1 h at room temperature in buffer B containing 6 M guanidine-HCl to denature proteins. For renaturation, the membrane was rinsed for 5 min and incubated in buffer B containing 0.04% Tween 40 for overnight at 4° C. For a non-denatured system, proteins were directly immobilized on a nitrocellulose membrane using a slot-blotter. The membrane was treated with Block Ace for 30 min at 4° C. and incubated with $^{32}$P-labeled protein probe in Block Ace supplemented with DNase I (18 μg/ml) and RNase A (60 μg/ml) for 4 h at 4° C. The filter membranes were washed four times each for 5 min with PBS containing 0.2% Triton X-100 and subjected to autoradiography analysis. The results are shown in FIG. 1.

On a Coomassie Brilliant Blue (CBB)-stained gel, a 48-kDa protein was observed when induced with IPTG (FIG. 1A, lane 2). Western blot analysis using anti-GST antibody showed that this protein was GST-fused MIP102 (data not shown). By using $^{32}$P-labeled ToMV-MP probe, a specific band was detected at the position corresponding to the induced protein (FIG. 1B, lane 2) while no such signal was observed in the un-induced lane (FIG. 1B, lane 1).

Subsequently, GST-MIP102 and GST were purified by using Glutathione Sepharose beads (FIG. 1C) and used for protein-binding assays with the same probe (FIG. 1D). Purified GST-MIP102 gave positive binding signal (FIG. 1D, lane 1) while purified GST did not (FIG. 1D, lane 2). This result indicated that MIP102 clone was isolated by a specific interaction with MP: it was not probed by GST-GST interaction.

Example 2

Analysis for cDNA and Genomic DNA of MIP102

The nucleotide sequence and its putative amino acid sequence of MIP102 cDNA were determined as follows.

Phage DNA was prepared from the plate lysate of each clone by using QIAGEN λ kit. For further analysis of the cDNA, phage DNA was digested with NotI to obtain the DNA fragment corresponding to pGEX-PUC-3T vector with cDNA insert. This DNA fragment was self-ligated to transform *E. coli*, from which the plasmid clone was recovered. The plasmid pGEX-Bc2 recovered from the phage clone MIP102 was used to produce the GST-fused protein GST-MIP102.

The nucleotide sequences were determined by using the following primers:

| | | |
|---|---|---|
| (5'-GCAAGCCACGTTTGGTGGTG-3' | SEQ ID NO:9 | pGEX1 primer |
| (5'-ATTTCCCCGAAAAGTGCCAC-3' | SEQ ID NO:10 | pGEX5 primer |
| (5'-GAGCTTCCTTCTTCTAAAGG-3' | SEQ ID NO:11 | Bc2F03 |
| (5'-GCTTCGATAGCTGGAATATT-3' | SEQ ID NO:12 | and Bc2R02 |

The nucleotide sequence of MIP102 cDNA (898 bp (excluding polyA)) is shown in FIG. 2. Homology searches using BLAST revealed that the putative protein was similar to a transcriptional coactivator KELP (75% identity) of *A. thaliana* (AtKELP; Cormack et al., (1998) Plant J. 14, 685–692) (FIG. 3). For assessment of percentage of peptide identity, GENETYX program was used. MIP102 had 36% identity to KIWI of *A. thaliana* (Cormack et al., (1998) Plant J. 14, 685–692) (FIG. 3). Related proteins were also found in several other taxonomically distinct organisms, such as human (PC4/p15, 36% identity) (Ge and Roeder, (1994) Cell 78, 513–523; Kretzschmar et al., supra) and *S. pombe* (protein having Protein ID CAB10003.1 in GenBank gene No. Z97185; 19% identity). Based on the N-terminal homology with AtKELP (FIG. 3), the first ATG codon was assumed to be the initiation codon for MIP102. The open reading frame (ORF) encoded a 165 amino acid polypeptide with a calculated molecular mass of 19,227 Da and a pI to 4.8. A highly conserved region implicated in single-stranded DNA-binding activity of PC4/p15 was identified (Kretzschmar et al., supra) (FIG. 3). The central region of MIP102 was rich in glutamine and glutamic acid (amino acid position 66 to 81). A homopolymeric glutamine stretch was reported to increase transcription factor potency (Gerber et al., (1994) Science 263, 808–811; Schwechheimer et al., (1998) Plant Mol. Biol. 36, 195–204).

To analyze the gene organization for MIP102, genomic DNA fragments were amplified by PCR and their nucleotide sequences were determined. Genomic DNA was isolated from leaves of *B. campestris* by phenol/SDS method (Kingston, (1997) Phenol/SDS method for plant RNA preparation. In "Current Protocols In Molecular Biology" (V B Chanda Eds) Vol. 1, pp. 4.3.1–4.3.3. John Wiley & Sons, Inc., New York). Genomic Southern hybridization was performed essentially as described by Sambrook et al., (1989) "Molecular Cloning A Laboratory Manual" Cold Spring Harbour Laboratory Press, Cold Spring Harbor, N.Y. The DNA samples (10 μg) were digested with appropriate restriction enzymes, fractioned through 1.0% agarose gel and transferred onto a positively charged nylon membrane (Millipore). The blot was hybridized with a $^{32}$P-labeled probe for 16 hours at 42° C. in a solution containing 50% formamide, 4.4×SSC, 20 mM sodium phosphate buffer (pH 6.8), 1× Denhardt's solution, 0.2% SDS and denatured salmon sperm DNA (0.1 mg/ml). The membrane was washed several times in 2×SSC containing 0.1% SDS at room temperature before the final washing for 30 min at 42° C. in 0.2×SSC containing 0.1% SDS.

Genomic DNA fragments corresponding to MIP102 cDNA were amplified by PCR using two sets of primers Bc2F04 (5'-GAAAACCCTAAAGATGGAG-3', SEQ ID NO:13) and BC2R02 (described above); Bc2F05 (5'-AATAAGCTTAACAGACGAAC-3', SEQ ID NO:14) and Bc2R07 (5'-GATTTTAAAAGATCATTTTTGTCAT-3', SEQ ID NO:15). The PCR products were cloned into a TA cloning vector pCR2.1 (Invitrogen) and the nucleotide sequences were determined for three independent clones using the vector primers: Forward-ABI (5'-TGTAAAAC-GACGGCCAGT-3', SEQ ID NO:16) and Reverse-1 (5'-GGAAACAGCTATGACCATG-3', SEQ ID NO:17) in addition to the internal primer Bc2F02 and Bc2R02 described above.

Figure 4:
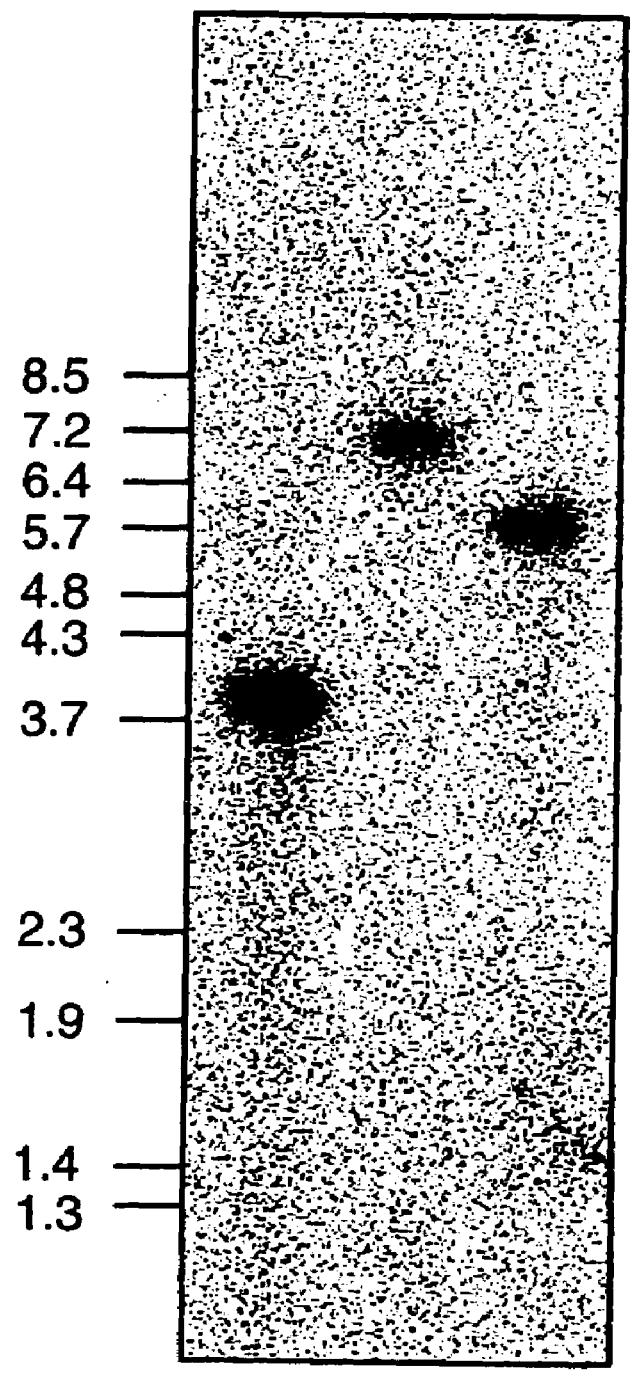

Comparison of the nucleotide sequence of the genomic DNA with that of cDNA revealed that the MIP102 gene contained two introns (FIG. 2) (73 bp (intron 1) and 278 bp (intron 2)). The locations of these introns were the same as those for AtKELP (Cormack et al., supra). To estimate the number of genes encoding MIP102 homologues in *B. campestris*, a Southern blot hybridization using a 440 bp fragment of MIP102 cDNA was conducted (FIG. 4). The DNA probe hybridized with one band in each lane, indicating that MIP102 is encoded by a single copy gene in *B. campestris*.

Example 3

Binding Assay with Deletion Mutants of MIP102

GST-fused MIP102with N- or C-terminal deletions were produced and used in a protein-binding assay as described in Example 1 to determine the domain of MIP102 that is responsible for MP binding.

The plasmid pGEX-P-Bc2 was derived from the phage clone MIP102 (described above). The pGEX-Bc2 BamHI-EcoRI fragment (842 bp) was inserted between BamHI and EcoRI sites of pGEX-6P-2 (Amersham Pharmacia Biotech) to produce pGEX-P-Bc2.

In order to construct pGEX-P-Bc2dN, the DNA fragment for the C-terminal half of MIP102 was amplified by PCR from pGEX-Bc2 using Bc2F02 primer (5'-AAYAARGART-TYGAYGAYGA-3' SEQ ID NO:18) and pGEX5 primer (described above), treated with T4 DNA polymerase and digested with NotI. The resultant 679-bp fragment was inserted between SmaI and NotI sites of pGEX-6P-2.

For the construction of pGEX-P-Bc2dC, the DNA fragment for the N-terminal half of MIP102 was amplified by PCR from pGEX-Bc2 using pGEX1 primer (described above) and Bc2R05 primer (5'-GAGACTCGAGTCATC-CCTCCTTAGCTCTTT-3' SEQ ID NO:19) and digested with BamHI plus XhoI. The resultant 331-bp fragment was inserted between BainHI and XhoI sites of pGEX-6P-2.

pGEX-P-Bc2 was used for the expression of GST-fused MIP102 (GST-MIP102). pGEX-P-Bc2dN was used for GST-fused MIP102 (GST-MIP102dN) with deletion of N-terminal 86 amino acid residues while pGEX-P-Bc2dC was used for GST-fused MIP102 (GST-MIP102dC) with deletion of C-terminal 79 amino acid residues. The coding sequences derived from PCR fragments were confirmed to have no errors.

As shown in FIG. 5A, $^{32}$P-labeled PKA-MP bound to GST-MIP102dC containing the N-terminal half (amino acid 1 to 86) of MIP102 (lane 3) as well as full length GST-MIP102 (amino acid 1 to 165) (lane 1). The double bands observed in the lane of GST-MIP102dC (FIG. 5B, lane 3) may be due to protein degradation near the C-terminus; the lower band with additional deletion showed the binding ability. In contrast, no MP-binding activity was observed in GST (lane 4) and GST-MIP102dN containing the C-terminal half (amino acid position 87 to 165) of MIP102 (lane 2). This result suggests that the N-terminal half of MIP102 contains the MP binding domain.

Example 4

Inhibition of Cell-to-Cell Movement by the N Terminal Region of MIP102

In order to allow for visual observation of ToMV movement, plasmid piL.G3 was used in which the coat protein (CP) gene of the virus genome was deleted and a green fluorescence protein (GFP) gene was inserted into the virus genome in place of the CP gene. This plasmid was obtained from Tetsuo Meshi of Kyoto University (Tamai and Meshi, Mol. Plant-Microbe Interact. (2001) 14, 126–134). Plasmid pART7-Bc2dC-HA was also prepared for expressing the C-terminal deletion MIP102(MIP102dC) obtained in Example 3. These preparation methods are described below.

In order to express MIP102dC, a plant expression binary vector pART7 was used (Andrew P. Gleave, Plant Molecular Biology (1992) 20, 1203–1207). DNA fragments for the N-terminal half of MIP102 were amplified by PCR from pGEX-Bc2 usign pGEX1 primer (described above) and Bc2R06HA primer (5'-TTGCTCTAGACTAAGCATAAT-CAGGAACATCATAAGGATA TCCCTCCT-TAGCTCTTTC-3' SEQ ID NO:20; this Bc2R06HA primer contains an HA tag sequence) and digested with SmaIplus XbaI. The resultant about 350-bp fragment had a tag coding a hemaglutinin epitope (HA) fragment sequence inserted at the C terminus thereof. This fragment was inserted between SinaI and XbaI sites downstream of the CaMV35S promoter of pART7-Bc2dC-HA. As a control plasmid, plasmid pART7-GUS which expresses GUS was also prepared.

Only plasmid piL.G3 or both of piL.G3 and pART7-Bc2dC-HA plasmids were subjected to a particle gun method using leaf pieces of true leaves of tobacco (*N. benthamiana*) to introduce these plasmids into tobacco cells. This introduction of genes into cells by the particle gun method was conducted using a BioRad gene introduction apparatus PDS-1000/He system in accordance with the manufacturer's instructions. Green fluorescence was observed under a fluorescence microscope. If the virus genome is transferred to neighboring cells, the green fluorescence protein is produced in the cells containing the transferred virus genome so that the cells emit green light (FIG. 6, "Multiple Cells"). In contrast, if there is no cell-to-cell movement of the virus, fluorescence occurs in only one cell (FIG. 6, "Single Cell"). Therefore, viral movement can be detected according to a difference in fluorescence.

Next, a plasmid piL.G3 having GFP inserted therein instead of the CP gene and a plasmid which expresses the MP binding region of GUS (pART-GUS) or MIP102 (pART7-Bc2dC-HA) were subjected to a particle gun method using leaf pieces of true leaves of tobacco, while changing the ratio of their amounts, to introduce these plasmids into tobacco cells. The result is shown in Table 1.

TABLE 1

Transient Gene Introduction into True Leaves of
*N. benthamiana* by Particle Gun

| Plasmid Combination | | Amount of DNA per Introduction | Number of Fluoresence Spots per Half Leaf[a] | | Multiple cells/ Total number[b] |
|---|---|---|---|---|---|
| | | | Only one cell emits light (portions without viral movement) | Multiple cells emits light (portions with viral movement) | |
| piL. G3 + (ToMV/GFP) | pART7-GUS (control) | 1.0 μg:2.5 μg | 19 | 133 | 0.87 ± 0.094 |
| piL. G3 + (ToMV/GFP) | pART7-Bc2dC-HA (MP binding region of MIP 102) | 1.0 μg:2.5 μg<br>0.5 μg:2.5 μg | 109<br>47 | 110<br>46 | 0.50 ± 0.11<br>0.49 ± 0.12 |

[a]The total number as a result of introduction into 3 to 4 leaves.
[b]Numbers following ± indicate standard deviations calculated from the results of introduction into 3 to 4 leaves The result shown in Table 1 revealed that expansion of green fluorescence, which is a sign of virus genome movement, is inhibited by the introduction of pART7-Bc2dC-HA. Therefore, it was considered that if a protein at the N terminus of MIP102 is expressed in cells, the function of viral MP is suppressed so viral movement is inhibited.

Figure 7:
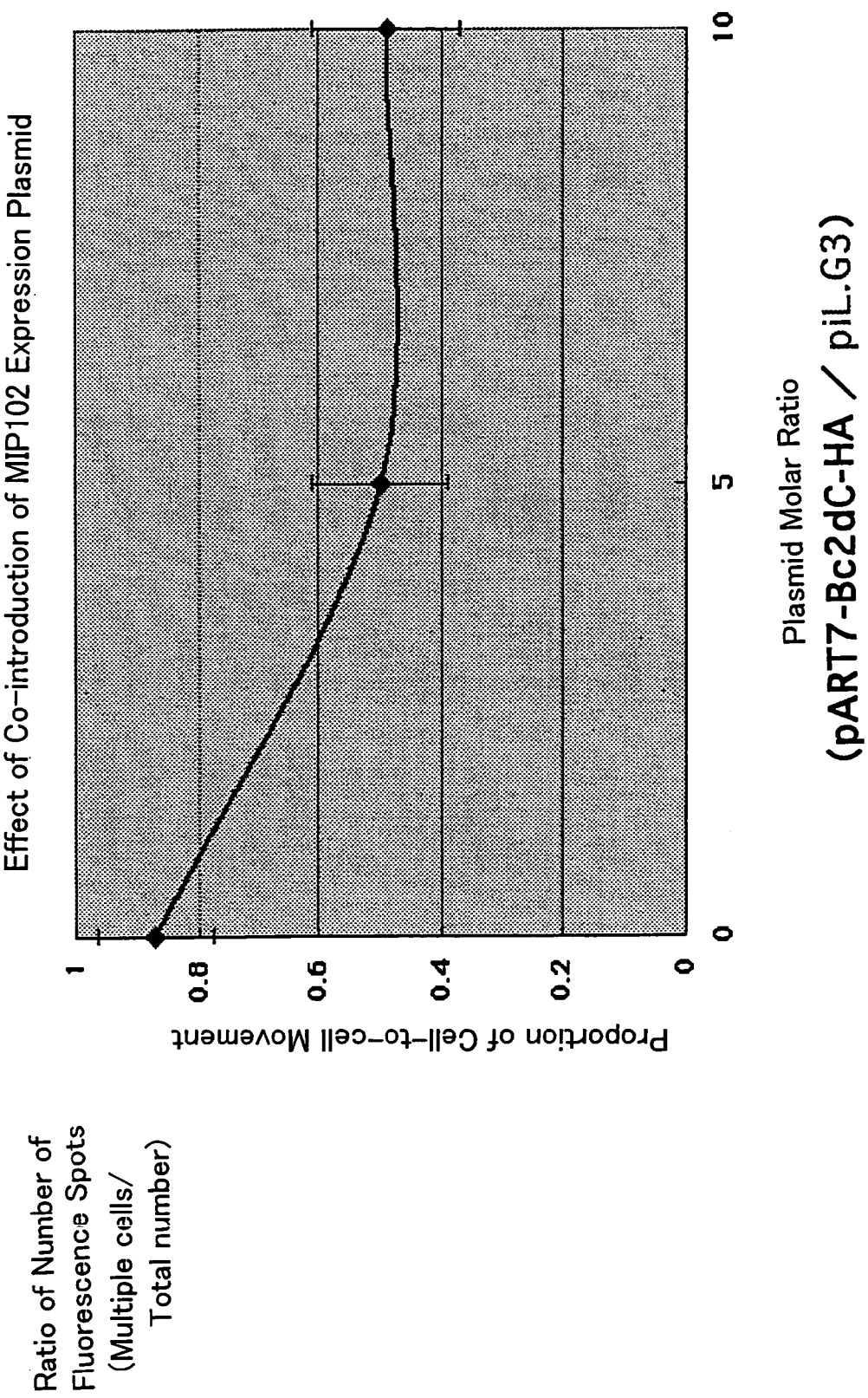

The rate of cell-to-cell movement was observed while varying the molar ratio of pART7-Bc2dC-HA and piL.G3. The result is shown in FIG. 7. In FIG. 7, the vertical axis indicates the rate of cell-to-cell movement represented by the fluorescence spot ratio (multiple cells/total number), while the horizontal axis indicates the molar ratio of plasmids (pART7-Bc2dC-HA/piL.G3). As pART7-Bc2dC-HA was relatively increased, expansion of green fluorescence to multiple cells was decreased, i.e., inhibition of movement was recognized.

Example 5

Effect of Co-Introduction of MIP102 Expression Plasmid When ER Localized GFP Expression Plasmid was Used The rate of cell-to-cell movement was observed while varying the molar ratio of pART7-Bc2dC-HA and piL.erG3 (ER localized GFP expression plasmid). piL. erG3 (ER localized GFP expression plasmid) was obtained from Tetsuo Meshi of Kyoto University (Jun Tamai and TetsuoMeshi, The Proceedings of Annual Meeting of Japanese Society of Plant Pathology (2000), Okayama University).

Figure 8:
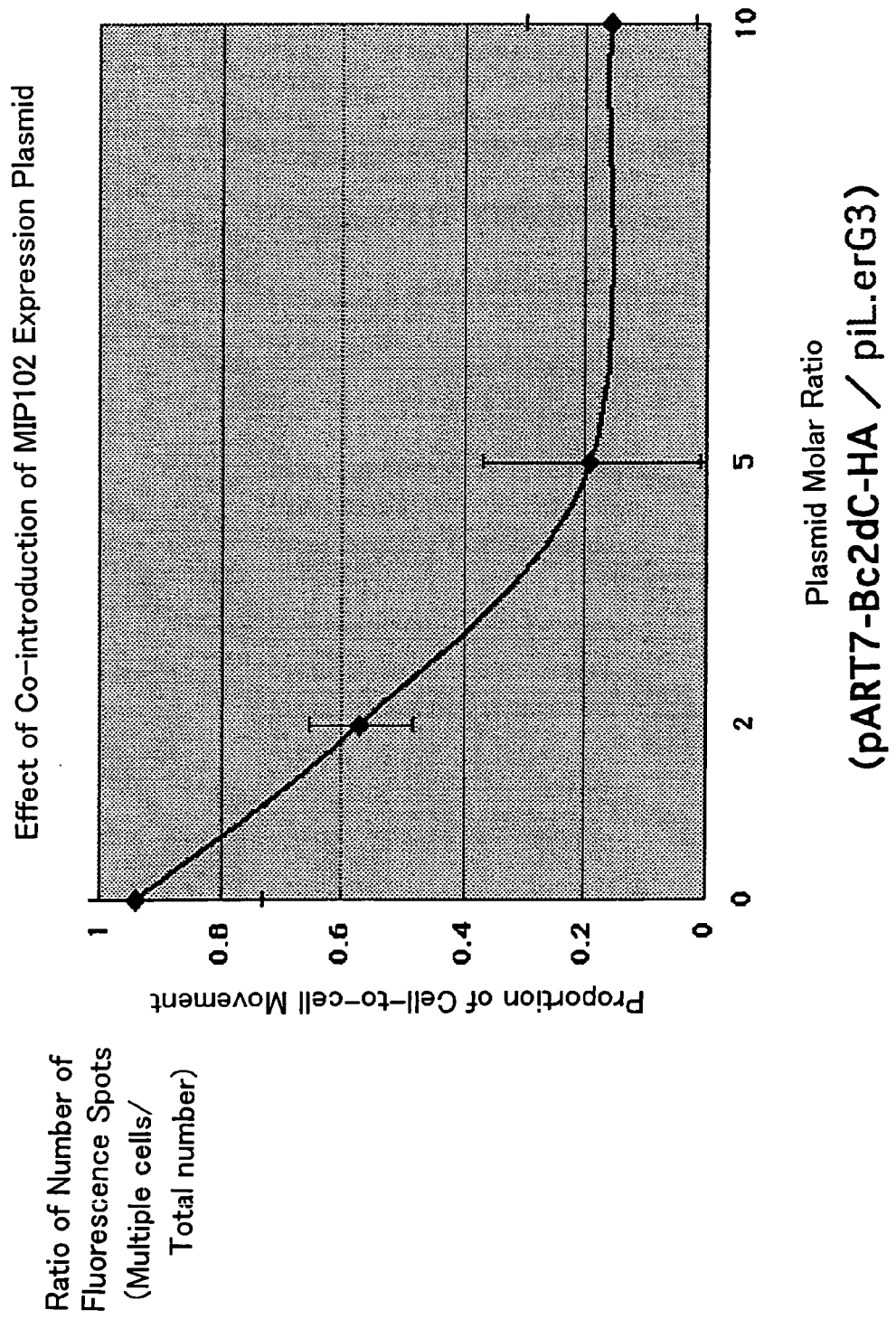

The result is shown in FIG. 8. In FIG. 8, the vertical axis indicates the rate of cell-to-cell movement represented by the fluorescence spot ratio (multiple cells/total number), while the horizontal axis indicates the molar ratio of plasmids (pART7-Bc2dC-HA/piL.erG3). As pART7-Bc2dC-HA was relatively increased, expansion of green fluorescence to multiple cells was decreased, i.e., inhibition of movement was recognized. Comparing FIG. 8 with FIG. 7, it was revealed that the degree of inhibition was greater when piL.erG3 (ER localized GFP expression plasmid) was used than when ER non-localized GFP expression plasmid (piL.G3) was used.

Example 6

Figure 9:
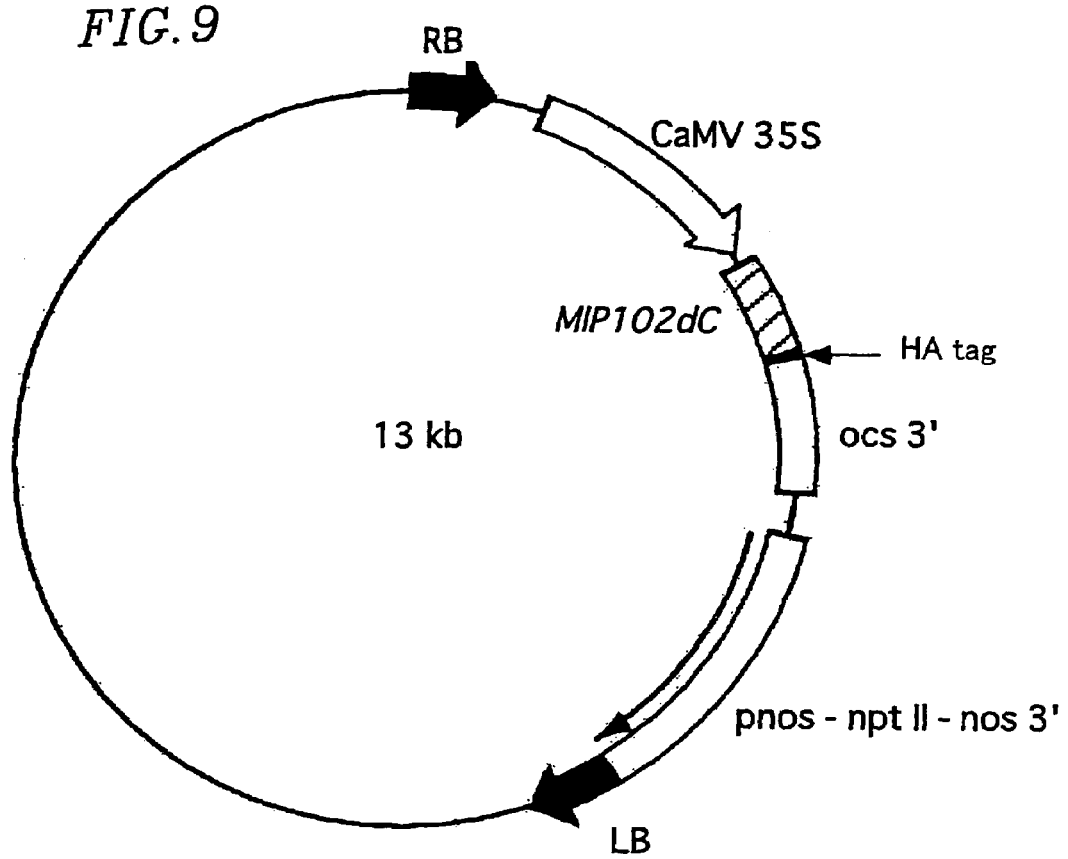

Construction of a Plasmid for Producing Transformed Plants by Introduction of MIP Gene and Preparation of Transformed Plants Using the Plasmid In order to produce transformed plants, phage DNA isolated from a MIP102 clone was used to construct an expression plasmid pART27-Bc2dC-HA.a which produces the N-terminal binding region of MIP102. A2.45-kb NotI fragment derived from pART7-Bc2dC-HA (described above) was inserted at the NotI site of pART27 (obtained from Andrew P. Gleave, Plant Molecular Biology (1992) 20, 1203–1207) to produce pART27-Bc2dC-HA.a. A construction diagram of this vector is shown in FIG. 9.

pART27-Bc2dC-HA.a was introduced into leaf pieces of tobacco by an *Agrobacterium* method. The *Agrobacterium* method was conducted in accordance with Nagel et al. (Microbiol. Lett., 67, 325 (1990)). The above-described expression vector was used to transform *Agrobacterium* by electroporation. Next, the transformed *Agrobacterium* was introduced into plant tissue by a leaf disc method (Rabo-Manyuaru [Laboratory Manual], Syokubutsu-Idenshi-no-Kino-Kaiseki [Functional Analysis of Plant Gene] Masaki Iwabuchi and Toshiro Shimura, eds., 1992, Maruzen, pp. 31–56). Every two weeks, the above-described leaf pieces were subcultured and screened for transformed tobacco cells based on the presence or absence of kanamycin resistance due to expression of the kanamycin resistance gene derived from pART27 which was introduced into the tobacco cells along with the above-described polynucleotide. The selected transformed tobacco cells were redifferentiated to plants.

The transformed tobacco leaf having the introduced MIP102 was pulverized in liquid nitrogen, followed by extraction in SDS-PAGE sample buffer at 100° C. for 4 min. The extract was subjected to SDS-polyacrylamide electrophoresis (SDS-PAGE, polyacrylamide gel concentration was 10 to 20%), followed by western blotting analysis by a commonly used method using anti-KELP antibodies (produced by immunizing rabbits with purified KELP derived from pGEX-P-KELP (its production is described in Example 9 below)) and anti-HA antibodies (obtained from MBL) as probes.

Figure 10:
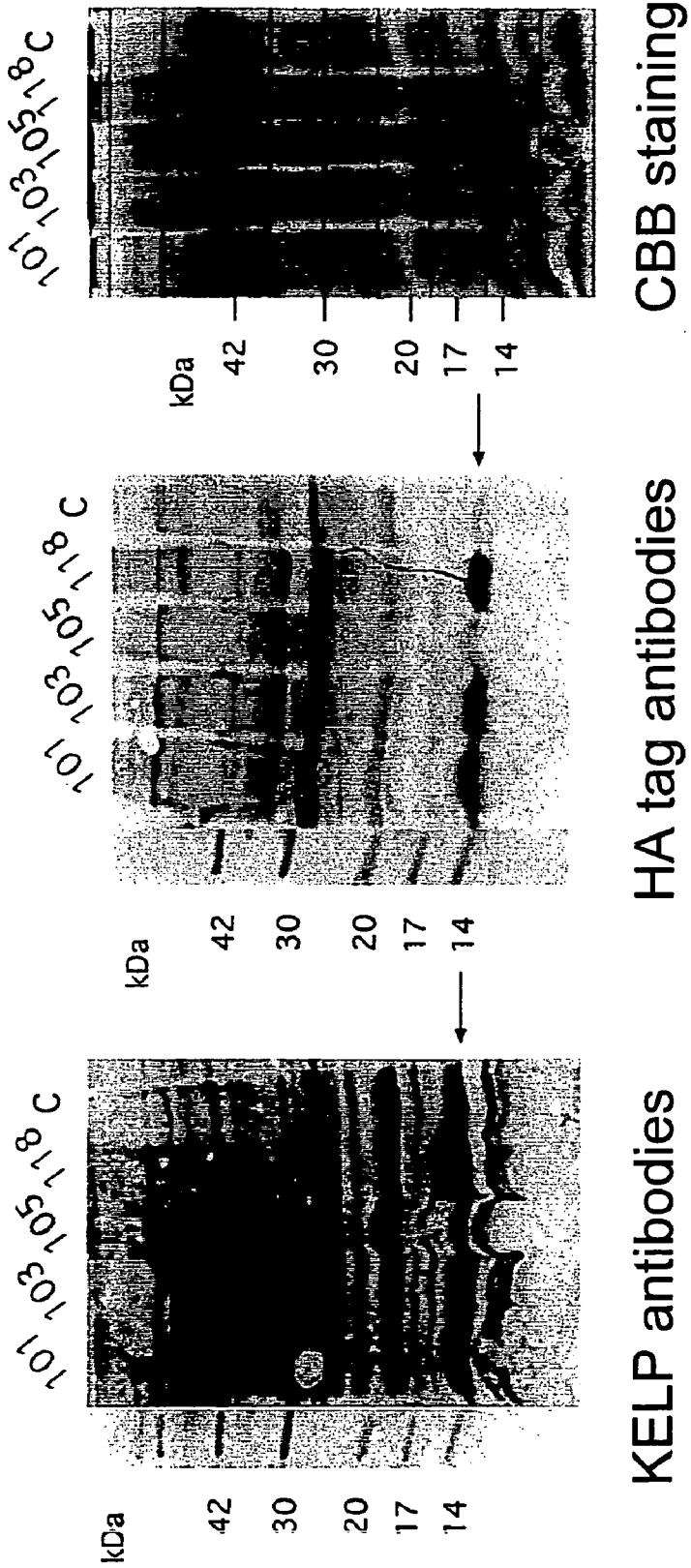

The result is shown in FIG. 10. (A) Coomassie Brilliant Blue (CBB)-stained gel, (B) the result of use of HA tag antibodies, and (C) the result of use of KELP antibodies. Of lanes in each result, the leftmost lane indicates a molecular mass marker and remaining lanes indicate transformed tobacco strains 101, 102, 105 and 118 from left in this order. The rightmost lane indicates a non-transformed tobacco (control). In these results, a specific band of 14 kDa, which is considered to correspond to MIP102, was detected for the transformed tobacco strains 101, 103 and 118, but not 105 and the non-transformed tobacco (control).

Example 7

Investigation of Viral Cell-To-Cell Movement due to ToMV-ΔCP/GFP Transcript Infection In order to observe viral movement in the transformed tobacco having the introduced MIP102, ToMV-ΔCP/GFP transcript product (RNA) was applied to leaves of the transformed tobacco strains having the introduced MIP102, 101, 103, 105 and 118, their regenerated plants 101r, 103r, 105r and 118r, and the non-transformed plant (SR1). Note that regenerated plants were produced from leaf pieces in accordance with a commonly used method. The application of the transcript was conducted as follows. pTL.G3 (obtained from Tetsuo Meshi of Kyoto University; in this plasmid, the T7 promoter is transcribed upstream of the virus gene instead of the CaMV $^{35}$S promoter of piL.G3) was treated with T7 RNA polymerase to obtain RNA transcripts. 1 μg of the RNA transcript was inoculated into tobacco leaves having a width of about 3 to 5 cm. After two days, the infected leaves were cut off and observed under a fluorescence microscope so as to observe fluorescence from GFP. The result is shown in Table 2.

TABLE 2

Infection of ToMV-ΔCP/GFP Transcript to Transformed Tobacco

| Transformed Tobacco Individual Number | Number of Fluorescence Spots | | Transformed Tobacco Individual Number | Number of Fluorescence Spots | |
|---|---|---|---|---|---|
| | One cell | Multiple cell | | One cell | Multiple cell |
| 101 | 0 | 0 | 101r | 0 | 0 |
| 103 | 0 | 0 | 103r | 0 | 0 |
| 105 | 0 | 51 | 105r | 0 | 3 |
| 118 | 0 | 0 | 118r | 0 | 0 |
| | | | Non-transformant 1 | 0 | 0 |
| | | | Non-transformant 2 | 0 | 6 |

| Transformed Tobacco Individual Number | Number of Fluorescence Spots | | Number of Fluorescence Spots | |
|---|---|---|---|---|
| | One cell | Multiple cell | One cell | Multiple cell |
| 101r | 0 | 1 | 0 | 4 |
| 103r | 0 | 0 | 0 | 0 |
| Non-transformant 1 | 0 | 48 | 0 | 45 |
| Non-transformant 2 | 0 | 108 | 0 | 108 |

101, 103 and 118 are MIP120dc high expression plants
101r, 103r, 105r, and 118r are regenerates from 101, 103, 105 and 118

As shown in Table 2, MIP102 was clearly expressed highly in Example 6 in the transformants 101, 103 and 118, and their regenerates 101r, 103r and 118r so that expansion of green fluorescence was suppressed in these plants. In the plant 105 without a high level of expression, its regenerate 105r, and the non-transformed plant (control), expansion of green fluorescence was observed. Thus, it was revealed that viral movement is inhibited in plants expressing MIP102.

Example 8

Investigation of Viral Infection by ToMV Particle Infection

To investigate whether resistance to ToMV infection was acquired by the transformed tobacco having the introduced MIP102, viral particle infection was conducted and then accumulation of viral coat protein (CP) in infected leaves and upper leaves was investigated. Leaves of the regenerates 101r, 103r, 105r and 118r of the transformed tobacco 101, 103, 105 and 118 having the introduced MIP102, and the non-transformed plant (control) were infected with 0.06 μg of ToMV viral particles. After 10 days, the infected leaves and the leaves present at upper positions (upper leaves) were cut off and pulverized in liquid nitrogen, followed by extraction in SDS-PAGE sample buffer at 100° C. for 4 min. The extract was subjected to SDS-polyacrylamide electrophoresis (SDS-PAGE, the polyacrylamide concentration was 10 to 20%) before staining the gel with Coomassie Brilliant Blue.

The result is shown in FIG. 11. The opposite end lanes indicate molecular mass markers, and the remaining lanes indicate transformed tobacco strains 101r, 102r, 105r and 118r (these were regenerates from transformed tobacco strains 101, 102, 105 and 118), and a non-transformed tobacco (SR1) from left in this order. For each strain, the left lane indicates upper leaves (U) while the right lane indicates infected leaves (I). A band indicated by an arrow corresponds to coat protein. This band was significantly observed in the infected leaves and upper leaves of the non-transformant SR1 and the transformant 105r which did not show a high level of expression of MIP102 in Example 6. The transformed strains 101r, 103r and 118r in which MIP102 was highly expressed and inhibition of viral movement was confirmed, accumulation of coat protein was reduced, so that virus resistance was expected.

Example 9

Binding Assay with AtKELP

To investigate whether ToMV MP binds to AtKELP having a high level of homology (75%) to MIP102, the cDNA for AtKELP was isolated from an *A. thaliana* cDNA library. A plasmid encoding GST-fused AtKELP (GST-AtKELP) was constructed and the purified fusion protein was used for a protein-binding assay with ToMV MP as the probe. The protein-binding assay was conducted as described in Example 3.

AtKELP expression plasmids were constructed as follows. The coding sequence of AtKELP (Cormack et al., supra) was amplified from *A thaliana* 5'-Stretch cDNA library (Clontech) by PCR using KELP-F01 primer (5'-ACAGGMTTCCTAAAAATGGAGAAAGAGA-3' SEQ ID NO:21) and KELP-F01 primer (5'-TTGCCTCGAGTCA-GACACGCGATTCCATTT-3' SEQ ID NO:22). The amplified 0.52-kb fragment was digested with EcoRI plus XhoI and inserted between EcoRI and XhoI sites of pGEX-6P-1 to produce pGEX-P-KELP. The coding sequence of KELP was confirmed to have no base change. TO add the phosphorylation sequence for protein kinase A, synthetic oligonucleotides KD-PKA1 (5'-GATCACGTCGTGCATCT-GTTG-3' SEQ ID NO:23) and KD-PKA2 (5'-GATCCAACAGATGCACGACGT-3' SEQ ID NO:24) were annealed and inserted into the BamHI site of pGEX-6P-1 to construct pGEX-6P1-3xPKA in which three sets of oligonucleotides were inserted in the appropriate orientation downstream of the GST ORF. For the construction of pGEX-P-3xPKA-KELP, 0.52-kb EcoRI-XhoI fragment of pGEX-P-KELP was cloned between EcoRI and XhoI sites of pGEX-6P1-3xPKA. pGEX-P-KELP and pGEX-P-3xPKA-KELP were used for expression of GST-AtKELP and GST-PKA-AtKELP, respectively.

As shown in FIG. 12, both GST-AtKELP (lane 1) and a positive control GST-MIP102 (lane 2) showed MP-binding activity, while a negative control GST did not show the activity.

Example 10

Binding Assay with MPs of CTMV-W and CMV

The present inventors also examined the binding ability of MIP102 and AtKELP to MPs of other plant viruses. In this case, the MPs of CTMV-W and CMV were used. Protein binding assay was conducted as described in Example 3.

CTMV-W MP expression plasmids were constructed as follows. The plasmid pTW62 (Shimamoto et al., (1998) Arch. Virol. 143, 1801–1813) containing the cDNA from a wasabi strain of crucifer tobamovirus (CTMV-W) was digested with SalI. The resultant 1.4-kb fragment containing the coding sequence of MP was inserted into SalI site of pAS2-1 (Clontech) in the same orientation as that of the Gal4 gene. The resultant plasmid was digested with NcoI plus BamHI, treated with Klenow fragment and self-ligated to produce pAS-W30K in which the ORF of MP was continuous to that of Gal4. The 1.4-kb BamHI-NotI fragment of this plasmid was inserted between BamHI and NotI sites of pGEX-5X-3 (Amersham Pharmacia Biotech) to produce pGEX-W30K. To adjust CTMV-W MP reading frame with that of GST, pGEX-W30K was further digested with BamHI, treated with Klenow fragment and self-ligated to generate pGEX-W30KfB, which was used for expression of GST-fused CTMV-W MP (GST-CTMVMP).

CMV MP expression plasmids were constructed as follows. The plasmid pUCMVO3 (Hayakawa et al., (1989) J. Gen. Virol. 70, 499–504) containing the RNA 3 cDNA derived from O strain of CMV (CMV-O) was digested with AvaI, treated with Klenow fragment and then digested with SalI to isolate 1.2-kb AvaI (blunted)-SalI fragment. This fragment containing the 3a ORF (MP) was inserted between SmaI and XhoI sites of pGEX-6P-1 to construct pGEX-P-CMVOMP, which encodes GST-fused CMV MP (GST-CMVMP).

As shown in FIG. 13, $^{32}$P-labeled PKA AtKELP bound to MPs of ToMV, CTMV-W, and CMV-O. When $^{32}$P-labeled MIP102 was used as a probe, similar binding activity was observed (data not shown).

The above-described examples illustratively describe various aspects of the present invention, how specific oligonucleotides of the present invention are produced, and how they are utilized. The present invention is not so limited.

INDUSTRIAL APPLICABILITY

A polynucleotide capable of conferring virus resistance, which can be utilized in plant breeding and a method for conferring virus resistance to plants using this polynucleotide are provided. Plants into which the polynucleotide is introduced to confer resistance to plant virus are also provided.

The invention claimed is:

1. A method for conferring resistance to a plant virus to a plant, comprising the step of introducing into the plant a polynucleotide encoding a protein that is expressed in the plant and interacts with a movement protein of the plant virus, wherein the protein encoded by the polynucleotide contains the amino acid sequence from position 1 to 86 of SEQ ID NO: 2.

2. The method according to claim 1, wherein the plant virus is Tobamovirus.

3. The method according to claim 1, wherein the plant virus is tomato mosaic virus (ToMV).

4. The method according to claim 1, wherein the polynucleotide contains the nucleotide sequence from position 14 to 271 of SEQ ID NO: 1.

5. A transformed plant produced by the method of claim 1.

6. The plant according to claim 5, wherein the plant is a monocotyledonous plant or a dicotyledonous plant.

7. The plant according to claim 6, wherein the plant is tobacco.

* * * * *

SEQUENCE LISTING

```
<160> NUMBER OF SEQ ID NOS: 32

<210> SEQ ID NO 1
<211> LENGTH: 913
<212> TYPE: DNA
<213> ORGANISM: Brassica campestris
<220> FEATURE:
<221> NAME/KEY: CDS
<222> LOCATION: (14)..(511)

<400> SEQUENCE: 1
gaaaacccta aag atg gag gaa gaa agc aag gcg aag atc gag gaa acg         49
            Met Glu Glu Glu Ser Lys Ala Lys Ile Glu Glu Thr
              1               5                  10 gtg cga gag att ctg aag gaa tcg gac atg acg gag atg aca gag ttc         97
Val Arg Glu Ile Leu Lys Glu Ser Asp Met Thr Glu Met Thr Glu Phe
       15                  20                  25 aag gtc cgt aac ctc gct tcg gag aga ctc ggc atc gat ctc tca gac       145
Lys Val Arg Asn Leu Ala Ser Glu Arg Leu Gly Ile Asp Leu Ser Asp
   30                  35                  40 aaa tct cac aag gcg ttc gta cgc ggc atc gtc aag tcg ttc ctc gaa       193
Lys Ser His Lys Ala Phe Val Arg Gly Ile Val Lys Ser Phe Leu Glu
45                  50                  55                  60 gaa gtg gag tcg aaa caa caa caa caa cag gac aag gaa gag gaa gag       241
```

-continued

```
Glu Val Glu Ser Lys Gln Gln Gln Gln Asp Lys Glu Glu Glu
             65                  70                  75 gaa gaa gaa gaa gaa aga gct aag gag gga aac aaa gag ttt gac gat    289
Glu Glu Glu Glu Glu Arg Ala Lys Glu Gly Asn Lys Glu Phe Asp Asp
                 80                  85                  90 gac ggc gat ctc atc att tgc agg ctg tcg gat aag agg aga gtg acg    337
Asp Gly Asp Leu Ile Ile Cys Arg Leu Ser Asp Lys Arg Arg Val Thr
             95                 100                 105 att cag gag ttt aga gga aag agt ttg gtt tcc atc aga gag tat tac    385
Ile Gln Glu Phe Arg Gly Lys Ser Leu Val Ser Ile Arg Glu Tyr Tyr
        110                 115                 120 aag aaa gac ggc aaa gag ctt cct tct tct aaa gga ata agc tta aca    433
Lys Lys Asp Gly Lys Glu Leu Pro Ser Ser Lys Gly Ile Ser Leu Thr
125                 130                 135                 140 gac gaa caa tgg tca acg ttc aag aaa aat att cca gct atc gaa gct    481
Asp Glu Gln Trp Ser Thr Phe Lys Lys Asn Ile Pro Ala Ile Glu Ala
                145                 150                 155 gct gtc aag aaa atg gaa tcg cgt gtc tga cgaacttgtg gttgattctg      531
Ala Val Lys Lys Met Glu Ser Arg Val
                160                 165 ctttcagaaa catatgcaag tgtcttgttg aatcagtggt gcaaaatgtt attgtgttta    591
tgtaacttat tttctttctt cggttggtcg taatgtgttt ctaagaggac ctggcgaacg    651
agccactatc atcagagtat tcagtagtac ttggccctgt tcgtttgctc acccaggtga    711
tccatctggg tgaagatgca aattgatgtt cgtttagtgt attataatgc tacatccaga    771
tgaatcaccc agctgaattc atctcaaatt ctcacccaaa tgaaggtgag tcttgatggt    831
gcatctggat acagatgcat ctagttcagt ccaaaataat aaatgacaaa aatgatcttt    891
taaaatcaaa aaaaaaaaaa aa                                            913
```

<210> SEQ ID NO 2
<211> LENGTH: 165
<212> TYPE: PRT
<213> ORGANISM: Brassica campestris

<400> SEQUENCE: 2

```
Met Glu Glu Glu Ser Lys Ala Lys Ile Glu Glu Thr Val Arg Glu Ile
1               5                   10                  15

Leu Lys Glu Ser Asp Met Thr Glu Met Thr Glu Phe Lys Val Arg Asn
            20                  25                  30

Leu Ala Ser Glu Arg Leu Gly Ile Asp Leu Ser Asp Lys Ser His Lys
        35                  40                  45

Ala Phe Val Arg Gly Ile Val Lys Ser Phe Leu Glu Glu Val Glu Ser
    50                  55                  60

Lys Gln Gln Gln Gln Gln Asp Lys Glu Glu Glu Glu Glu Glu Glu Glu
65                  70                  75                  80

Glu Arg Ala Lys Glu Gly Asn Lys Glu Phe Asp Asp Gly Asp Leu
                85                  90                  95

Ile Ile Cys Arg Leu Ser Asp Lys Arg Arg Val Thr Ile Gln Glu Phe
            100                 105                 110

Arg Gly Lys Ser Leu Val Ser Ile Arg Glu Tyr Tyr Lys Lys Asp Gly
        115                 120                 125

Lys Glu Leu Pro Ser Ser Lys Gly Ile Ser Leu Thr Asp Glu Gln Trp
    130                 135                 140

Ser Thr Phe Lys Lys Asn Ile Pro Ala Ile Glu Ala Ala Val Lys Lys
145                 150                 155                 160
```

```
Met Glu Ser Arg Val
              165

<210> SEQ ID NO 3
<211> LENGTH: 9
<212> TYPE: DNA
<213> ORGANISM: Artificial
<220> FEATURE:
<223> OTHER INFORMATION: phosphorylated oligonucleotide adapter-1

<400> SEQUENCE: 3 aggtgctgg                                                             9

<210> SEQ ID NO 4
<211> LENGTH: 12
<212> TYPE: DNA
<213> ORGANISM: Artificial
<220> FEATURE:
<223> OTHER INFORMATION: phosphorylated oligonucleotide adapter-2

<400> SEQUENCE: 4
ccagcacctg ca                                                        12

<210> SEQ ID NO 5
<211> LENGTH: 21
<212> TYPE: DNA
<213> ORGANISM: Artificial
<220> FEATURE:
<223> OTHER INFORMATION: synthetic oligonucleotide 30K-PKA1

<400> SEQUENCE: 5
aattcgtcgt gcatctgttg c                                              21

<210> SEQ ID NO 6
<211> LENGTH: 21
<212> TYPE: DNA
<213> ORGANISM: Artificial
<220> FEATURE:
<223> OTHER INFORMATION: synthetic oligonucleotide 30K-PKA2

<400> SEQUENCE: 6
aattgcaaca gatgcacgac g                                              21

<210> SEQ ID NO 7
<211> LENGTH: 27
<212> TYPE: PRT
<213> ORGANISM: Artificial
<220> FEATURE:
<223> OTHER INFORMATION: synthetic vector

<400> SEQUENCE: 7

Gln Val Ala Leu Phe Gly Glu Met Cys Ala Glu Pro Leu Phe Val Tyr
1               5                   10                  15

Phe Ser Lys Tyr Ile Gln Ile Cys Ile Arg Ser
            20                  25

<210> SEQ ID NO 8
<211> LENGTH: 7
<212> TYPE: PRT
<213> ORGANISM: Artificial
<220> FEATURE:
<223> OTHER INFORMATION: synthetic vector

<400> SEQUENCE: 8

Leu Glu Arg Pro His Arg Asp
1               5
```

<210> SEQ ID NO 9
<211> LENGTH: 20
<212> TYPE: DNA
<213> ORGANISM: Artificial
<220> FEATURE:
<223> OTHER INFORMATION: pGEX1 primer

<400> SEQUENCE: 9
gcaagccacg tttggtggtg                                         20

<210> SEQ ID NO 10
<211> LENGTH: 20
<212> TYPE: DNA
<213> ORGANISM: Artificial
<220> FEATURE:
<223> OTHER INFORMATION: pGEX5 primer

<400> SEQUENCE: 10
atttccccga aaagtgccac                                         20

<210> SEQ ID NO 11
<211> LENGTH: 20
<212> TYPE: DNA
<213> ORGANISM: Artificial
<220> FEATURE:
<223> OTHER INFORMATION: Bc2F03 primer

<400> SEQUENCE: 11
gagcttcctt cttctaaagg                                         20

<210> SEQ ID NO 12
<211> LENGTH: 20
<212> TYPE: DNA
<213> ORGANISM: Artificial
<220> FEATURE:
<223> OTHER INFORMATION: Bc2R02 primer

<400> SEQUENCE: 12
gcttcgatag ctggaatatt                                         20

<210> SEQ ID NO 13
<211> LENGTH: 19
<212> TYPE: DNA
<213> ORGANISM: Artificial
<220> FEATURE:
<223> OTHER INFORMATION: Bc2F04 primer

<400> SEQUENCE: 13
gaaaacccta aagatggag                                          19

<210> SEQ ID NO 14
<211> LENGTH: 20
<212> TYPE: DNA
<213> ORGANISM: Artificial
<220> FEATURE:
<223> OTHER INFORMATION: Bc2F05 primer

<400> SEQUENCE: 14
aataagctta acagacgaac                                         20

<210> SEQ ID NO 15
<211> LENGTH: 25
<212> TYPE: DNA
<213> ORGANISM: Artificial
<220> FEATURE:

<223> OTHER INFORMATION: Bc2R07 primer

<400> SEQUENCE: 15
gattttaaaa gatcattttt gtcat                                              25

<210> SEQ ID NO 16
<211> LENGTH: 18
<212> TYPE: DNA
<213> ORGANISM: Artificial
<220> FEATURE:
<223> OTHER INFORMATION: Forward-ABI primer

<400> SEQUENCE: 16
tgtaaaacga cggccagt                                                      18

<210> SEQ ID NO 17
<211> LENGTH: 19
<212> TYPE: DNA
<213> ORGANISM: Artificial
<220> FEATURE:
<223> OTHER INFORMATION: Reverse-1 primer

<400> SEQUENCE: 17
ggaaacagct atgaccatg                                                     19

<210> SEQ ID NO 18
<211> LENGTH: 20
<212> TYPE: DNA
<213> ORGANISM: Artificial
<220> FEATURE:
<223> OTHER INFORMATION: Bc2F02 primer

<400> SEQUENCE: 18
aayaargart tygaygayga                                                    20

<210> SEQ ID NO 19
<211> LENGTH: 30
<212> TYPE: DNA
<213> ORGANISM: Artificial
<220> FEATURE:
<223> OTHER INFORMATION: Bc2R05 primer

<400> SEQUENCE: 19
gagactcgag tcatccctcc ttagctcttt                                         30

<210> SEQ ID NO 20
<211> LENGTH: 58
<212> TYPE: DNA
<213> ORGANISM: Artificial
<220> FEATURE:
<223> OTHER INFORMATION: Bc2R06HA primer

<400> SEQUENCE: 20
ttgctctaga ctaagcataa tcaggaacat cataaggata tccctcctta gctctttc          58

<210> SEQ ID NO 21
<211> LENGTH: 29
<212> TYPE: DNA
<213> ORGANISM: Artificial
<220> FEATURE:
<223> OTHER INFORMATION: KELP-F01 primer

<400> SEQUENCE: 21
acaggaattc ctaaaaatgg agaaagaga                                          29

<210> SEQ ID NO 22
<211> LENGTH: 30
<212> TYPE: DNA
<213> ORGANISM: Artificial
<220> FEATURE:
<223> OTHER INFORMATION: KELP-RO1 primer

<400> SEQUENCE: 22
ttgcctcgag tcagacacgc gattccattt                30

<210> SEQ ID NO 23
<211> LENGTH: 21
<212> TYPE: DNA
<213> ORGANISM: Artificial
<220> FEATURE:
<223> OTHER INFORMATION: synthetic oligonucleotide KD-PKA1

<400> SEQUENCE: 23
gatcacgtcg tgcatctgtt g                         21

<210> SEQ ID NO 24
<211> LENGTH: 21
<212> TYPE: DNA
<213> ORGANISM: Artificial
<220> FEATURE:
<223> OTHER INFORMATION: synthetic oligonucleotide KD-PKA2

<400> SEQUENCE: 24
gatccaacag atgcacgacg t                         21

<210> SEQ ID NO 25
<211> LENGTH: 165
<212> TYPE: PRT
<213> ORGANISM: Arabidopsis thaliana

<400> SEQUENCE: 25

Met Glu Lys Glu Thr Lys Glu Lys Ile Glu Lys Thr Val Ile Glu Ile
1               5                   10                  15

Leu Ser Glu Ser Asp Met Lys Glu Ile Thr Glu Phe Lys Val Arg Lys
            20                  25                  30

Leu Ala Ser Glu Lys Leu Ala Ile Asp Leu Ser Glu Lys Ser His Lys
        35                  40                  45

Ala Phe Val Arg Ser Val Val Glu Lys Phe Leu Asp Glu Glu Arg Ala
    50                  55                  60

Arg Glu Tyr Glu Asn Ser Gln Val Asn Lys Glu Glu Asp Gly Asp
65                  70                  75                  80

Lys Asp Cys Gly Lys Gly Asn Lys Glu Phe Asp Asp Gly Asp Leu
                85                  90                  95

Ile Ile Cys Arg Leu Ser Asp Lys Arg Arg Val Thr Ile Gln Glu Phe
            100                 105                 110

Lys Gly Lys Ser Leu Val Ser Ile Arg Glu Tyr Tyr Lys Lys Asp Gly
        115                 120                 125

Lys Glu Leu Pro Thr Ser Lys Gly Ile Ser Leu Thr Asp Glu Gln Trp
    130                 135                 140

Ser Thr Phe Lys Lys Asn Met Pro Ala Ile Glu Asn Ala Val Lys Lys
145                 150                 155                 160

Met Glu Ser Arg Val
                165

<210> SEQ ID NO 26
<211> LENGTH: 23

```
<212> TYPE: PRT
<213> ORGANISM: Brassica campestris

<400> SEQUENCE: 26

Leu Val Ser Ile Arg Glu Tyr Tyr Lys Lys Asp Gly Lys Glu Leu Pro
 1               5                  10                  15

Ser Ser Lys Gly Ile Ser Leu
            20

<210> SEQ ID NO 27
<211> LENGTH: 23
<212> TYPE: PRT
<213> ORGANISM: Arabidopsis thaliana

<400> SEQUENCE: 27

Leu Val Ser Ile Arg Glu Tyr Tyr Lys Lys Asp Gly Lys Glu Leu Pro
 1               5                  10                  15

Thr Ser Lys Gly Ile Ser Leu
            20

<210> SEQ ID NO 28
<211> LENGTH: 23
<212> TYPE: PRT
<213> ORGANISM: Arabidopsis thaliana

<400> SEQUENCE: 28

Trp Ile Asp Ile Arg Glu Phe Tyr Val Lys Asp Gly Lys Thr Leu Pro
 1               5                  10                  15

Gly Lys Lys Gly Ile Ser Leu
            20

<210> SEQ ID NO 29
<211> LENGTH: 23
<212> TYPE: PRT
<213> ORGANISM: Schizosaccharomyces pombe

<400> SEQUENCE: 29

Tyr Val His Ile Arg Glu Tyr Tyr Glu Lys Asp Gly Asp Met Leu Pro
 1               5                  10                  15

Gly Lys Lys Gly Ile Ala Leu
            20

<210> SEQ ID NO 30
<211> LENGTH: 25
<212> TYPE: PRT
<213> ORGANISM: Caenorhabditis elegans

<400> SEQUENCE: 30

Tyr Val Asn Ile Arg Glu Tyr Tyr Ile Asp Arg Asp Ser Gln Lys Met
 1               5                  10                  15

Met Pro Ser Arg Lys Gly Ile Ser Leu
            20                  25

<210> SEQ ID NO 31
<211> LENGTH: 24
<212> TYPE: PRT
<213> ORGANISM: Homo sapiens

<400> SEQUENCE: 31

Leu Ile Asp Ile Arg Glu Tyr Trp Met Asp Pro Glu Gly Glu Met Lys
 1               5                  10                  15
```

-continued

```
Pro Gly Arg Lys Gly Ile Ser Leu
            20

<210> SEQ ID NO 32
<211> LENGTH: 5
<212> TYPE: PRT
<213> ORGANISM: Artificial
<220> FEATURE:
<223> OTHER INFORMATION: synthetic

<400> SEQUENCE: 32

Arg Arg Ala Ser Val
1               5
```